United States Patent
Verheesen et al.

(10) Patent No.: US 9,380,781 B2
(45) Date of Patent: Jul. 5, 2016

(54) COMPOSITIONS FOR SEED TREATMENT

(75) Inventors: Peter Verheesen, Mariakerke (BE); Chris De Jonghe, Aartselaar (BE); Erik Jongedijk, Lokeren (BE)

(73) Assignee: Agrosavfe N.V., Ghent (BE)

( * ) Notice: Subject to any disclaimer, the term of this patent is extended or adjusted under 35 U.S.C. 154(b) by 412 days.

(21) Appl. No.: 13/819,331

(22) PCT Filed: Aug. 26, 2011

(86) PCT No.: PCT/EP2011/064740
§ 371 (c)(1),
(2), (4) Date: May 11, 2013

(87) PCT Pub. No.: WO2012/025621
PCT Pub. Date: Mar. 1, 2012

(65) Prior Publication Data
US 2013/0225403 A1    Aug. 29, 2013

Related U.S. Application Data

(60) Provisional application No. 61/402,307, filed on Aug. 26, 2010.

(30) Foreign Application Priority Data

Sep. 7, 2010  (EP) .................................... 10175543

(51) Int. Cl.
| | | |
|---|---|---|
| C07K 16/14 | (2006.01) | |
| A01N 37/46 | (2006.01) | |
| C07K 16/16 | (2006.01) | |
| C07K 16/18 | (2006.01) | |
| A01G 1/00 | (2006.01) | |
| G01N 33/569 | (2006.01) | |

(52) U.S. Cl.
CPC ............... *A01N 37/46* (2013.01); *A01G 1/001* (2013.01); *C07K 16/14* (2013.01); *C07K 16/16* (2013.01); *C07K 16/18* (2013.01); *G01N 33/56961* (2013.01); *C07K 2317/22* (2013.01); *C07K 2317/569* (2013.01)

(58) Field of Classification Search
None
See application file for complete search history.

(56) References Cited

U.S. PATENT DOCUMENTS

| | | | |
|---|---|---|---|
| 2,651,883 | A | 9/1953 | Hedrick et al. |
| 3,316,676 | A | 5/1967 | Legal, Jr. et al. |
| 3,598,565 | A | 8/1971 | Graves |
| 3,707,807 | A | 1/1973 | Graves |
| 4,245,432 | A | 1/1981 | Dannelly |
| 5,004,699 | A | 4/1991 | Winters |
| 5,876,739 | A | 3/1999 | Turnblad et al. |
| 6,180,141 | B1 | 1/2001 | Lemercier et al. |
| 6,228,599 | B1 * | 5/2001 | Knox et al. ..................... 435/7.1 |
| 7,494,526 | B2 | 2/2009 | Yavitz |
| 8,598,081 | B2 * | 12/2013 | Jongedijk et al. .......... 504/116.1 |
| 2005/0107256 | A1 * | 5/2005 | Barnwell et al. ............... 504/117 |

FOREIGN PATENT DOCUMENTS

| | | |
|---|---|---|
| WO | 90/06954 A1 | 6/1990 |
| WO | 9217786 A1 | 10/1992 |
| WO | 9404678 | 3/1994 |
| WO | 9411511 A1 | 5/1994 |
| WO | 9825445 | 6/1998 |
| WO | 9937681 | 7/1999 |
| WO | 0024884 | 5/2000 |
| WO | 0043507 | 7/2000 |
| WO | 0140310 | 6/2001 |
| WO | 0190190 | 11/2001 |
| WO | 02085945 | 10/2002 |
| WO | 03025020 | 3/2003 |
| WO | 03031477 | 4/2003 |
| WO | 03035694 | 5/2003 |
| WO | 03074660 A2 | 9/2003 |
| WO | 2004004453 | 1/2004 |
| WO | 2004031379 A1 | 4/2004 |
| WO | WO 2005001098 A1 * | 1/2005 |
| WO | 2005102045 | 11/2005 |
| WO | 2006112700 | 10/2006 |
| WO | 2004049794 | 3/2007 |
| WO | 2007103076 | 9/2007 |
| WO | 2007118670 | 10/2007 |
| WO | 2010066740 | 6/2010 |
| WO | 2010107312 | 9/2010 |
| WO | 2011/124612 A1 | 10/2011 |
| WO | 2012/025619 | 3/2012 |
| WO | 2012025621 | 3/2012 |

OTHER PUBLICATIONS

Janeway et al., Immunobiology, 3rd edition, 1997, Garland Publishing Inc. New York, pp. 3:1-3:11.*
Rudikoff et al., Proc Natl Acad Sci U S A. Mar. 1982;79(6):1979-83.*
Ewert et al., Biochemistry. Mar. 19, 2002;41(11):3628-36.*
De Hoff et al., Mol Genet Genomics. Jul. 2009;282(1):1-15. doi: 10.1007/s00438-009-0460-8. Epub Jun. 2, 2009.*
Knox, JP. FASEB J. Aug. 1995;9(11):1004-12.*
Casero et al.; The monoclonal antibody JIM5 indicates patterns of pectin deposition in relation to pit fields at the plasma-membrane-face of tomato pericarp cell walls; Protoplasma; vol. 188; No. 1-2; 1995; pp. 133-137.

(Continued)

*Primary Examiner* — Michael Szperka
(74) *Attorney, Agent, or Firm* — TraskBritt, P.C.

(57) ABSTRACT

Described is a composition for seed treatment comprising a plant seed-binding protein, preferably an antigen-binding plant seed-binding protein. In one embodiment, the seed-binding protein is binding a polysaccharide, preferably pectin. Further described is the use of a plant seed-binding protein to bind a plant-enhancing agent to a plant seed, and to a method for treating plant seeds.

26 Claims, 5 Drawing Sheets

(56) References Cited

OTHER PUBLICATIONS

Pattathil et al.; A Comprehensive Toolkit of Plant Cell Wall Glycan-Directed Monoclonal Antibodies; Plant Physiology; vol. 153; No. 2; Jun. 2010; pp. 514-525.
International Search Report PCT/EP2011/064740 dated Dec. 12, 2011.
Pattathil et al.; Supplemental Materials: A Comprehensive Toolkit of Plant Cell Wall Glycan-Directed Monoclonal Antibodies; Plant Physiology; Jun. 2010; pp. 1-17.
Van Der Linden et al.; Comparison of physical chemical properties of llama VHH antibody fragments and mouse monoclonal antibodies; Biochimica et Biophysica Acta. Protein Structure and Molecular Enzymology; vol. 1431, No. 1; Apr. 12, 1999; pp. 37-46.
Stijlemans B et al., "Efficient targeting of conserved cryptic epitopes of infectious agents by single domain antibodies. African trypanosomes as paradigm", Journal of Biological Chemistry, American Society for Biochemistry and Molecular Biology, Inc., vol. 279, No. 2, pp. 1256-1261, Mar. 10, 2003.
Agdour, Siham et al., Production and characterization of the recombinant wheat chitinase Wch1 and generation of chitin-specific antibodies, Master of Science, dated Aug. 31, 2007.
Joshi, Mohan Chandra et al., An Insecticidal GroEL Protein with Chitin Binding Activity from Xenorhabdus nematophila, the Journal of Biological Chemistry, Oct. 17, 2008, pp. 28287-28296, vol. 283, No. 42.
Secundino, N. F C et al., Lutzomyia longipalpis Peritrophic Matrix: Formation, Structure, and Chemical Composition, Journal of Medical Entomology, 2005, pp. 928-938, vol. 42, No. 6.
Willats et al., In-situ analysis of pectic polysaccharides in seed mucilage and at the roof surface of Arabidopsis thaliana, Planta, 2001, pp. 37-44, vol. 213, Springer-Verlag.

* cited by examiner

E1  Lime pectin, DE 11%

F1  Lime pectin, DE 43%

G1  Lime pectin, DE 0%

H1  Lime pectin, DE 16%

I2  RGII enriched pectin (red wine)

I3  Seed mucilage (Arabidopsis)

H4  RGI #5 (potato)

COMPOSITIONS FOR SEED TREATMENT

CROSS-REFERENCE TO RELATED APPLICATIONS

This application is a national phase entry under 35 U.S.C. §371 of International Patent Application PCT/EP2011/064740, filed Aug. 26, 2011, designating the United States of America and published in English as International Patent Publication WO 2012/025621 A1 on Mar. 1, 2012, which claims the benefit under Article 8 of the Patent Cooperation Treaty and under 35 U.S.C. §119(e) to U.S. Provisional Patent Application Ser. No. 61/402,307, filed Aug. 26, 2010, and to European Patent Application Serial No. 10175543.7, filed Sep. 7, 2010.

TECHNICAL FIELD

The disclosure relates to a composition for seed treatment comprising a plant seed-binding protein, preferably an antigen-binding plant seed-binding protein. In one embodiment, the seed-binding protein is binding a polysaccharide, preferably pectin. The invention relates further to the use of a plant seed-binding protein to bind a plant-enhancing agent to a plant seed, and to a method for treating plant seeds.

BACKGROUND

Seed-borne and early season diseases and pests pose devastating consequences to crop production if not adequately managed, as germinating seeds and emerging plants are particularly vulnerable to damage during early growth stages. Therefore, it is of utmost importance to provide appropriate protection to seeds and emerging plants from seed- and soil-borne pests and diseases. Traditionally, this has been achieved by applying pesticides directly into the soil, mostly under the form of granules. In an effort to reduce the impact of pesticides on public health and on environment, more recent advances in pest control include the application of pesticides directly onto the seeds under the form of compositions for seed treatment. A broad spectrum of technologies is being practiced nowadays to treat seeds in order to provide seed and plant protection and to improve the establishment of healthy crops. These methods for seed treatment include dressing, coating and pelleting of the seeds.

It remains technically challenging to prepare suitable compositions for seed treatment as such compositions should satisfy a whole range of requirements: the composition should adhere well to the surface of the seed to avoid easy wash-off of the active substance and to reduce dust formation during sowing, but should at the same time not result in making the seeds sticky, such that the seeds would adhere to each other and form conglomerates, or such that seed storage or handling could be hampered by seeds sticking to the wall of the storage container or by seeds clogging sowing equipment or by reduced flowability of the seeds through a seed planter, resulting in uneven seed planting. Moreover, the composition should not reduce the storage life or life span of treated seeds, the composition should not adversely affect the germination of the seeds, e.g., by impairing water and gas exchange from the environment to the seed once planted and the composition should not cause damage to the seed or the seedling due to the phytotoxicity of the active substances present in the composition for seed treatment.

In order to ensure accessibility of the seed upon germination, U.S. Pat. No. 2,651,883, U.S. Pat. No. 3,707,807 and U.S. Pat. No. 3,598,565 describe methods for seed treatment using water-soluble polymer coatings, so that the coating would dissolve to allow exposure of the seeds to the environment for development. U.S. Pat. No. 3,316,676 and U.S. Pat. No. 4,245,432 relate to water-insoluble but water-sensitive seed coatings, the integrity of which is destroyed or which disintegrate when in contact with water. Although these methods allow for a good contact between the seed and its environment during germination, the rapid dissolution or disintegration of the seed coating will also cause a quick loss of the active substances contained in the seed coating. U.S. Pat. No. 5,876,739 describes a non-phytotoxic polymer-based film coating for seeds, which allows controlled release of an insecticide over a prolonged period of time. WO 2007/103076 and WO 2010/107312 also describe that polymer-based coating of seeds can be lubricated to facilitate flowability during planting. However, the coating is still based on aspecific sticking of the polymer to the seed, and plant-enhancing agents should be incorporated in a surplus of coating material.

There is still a need for a composition for seed treatment that allows a specific binding of the plant-enhancing agent to the plant seed, resulting in a thin and permeable coating, without unwanted loss of the plant-enhancing agent in the environment.

DISCLOSURE

Surprisingly, we found that incorporation of a plant seed-binding protein in a composition for seed treatment can solve the above-mentioned technical problems. Seed-binding proteins, preferably, antigen-binding proteins that are binding specifically to seeds when comprised in compositions for seed treatment, result in compositions that can strongly and specifically bind plant-enhancing agents beneficial to the seeds, while still allowing interaction between the seed and its environment to interfere as little as possible with the natural germination process.

In one preferred embodiment, the seed-binding protein comprised in the composition for seed treatment is a polysaccharide-binding protein. Polysaccharide-binding proteins are known to the person skilled in the art and include, but are not limited to, lectins and antigen-binding proteins.

The seed-binding protein can be coupled directly to a plant-enhancing agent, or it can be coupled to a carrier comprising the plant-enhancing agent. The latter case is especially useful when a slow release of the compound is wanted, over a certain period of time.

A first aspect hereof is a composition for seed treatment, comprising a plant seed-binding protein.

The terms "seed" and "plant seed" are used interchangeably herein and mean a seed that had been harvested from a plant grown in a greenhouse, in a nursery or on the field, that had been removed from the plant and separated from any cob, stalk, outer husk and surrounding pulp or other non-seed plant material. In addition to a plant seed as such, the terms "seed" and "plant seed" are also meant to include a germinating seed, a rootstock, plant cuttings used for vegetative propagation of a plant and plant parts used for propagation such as rhizomes, potato tubers or flower bulbs. Preferably, the terms "seed" and "plant seed" mean a seed that had been harvested from a plant grown in a greenhouse, in a nursery or on the field, that had been removed from the plant and separated from any cob, stalk, outer husk and surrounding pulp or other non-seed plant material. The plant seed may be further sorted for size, weight or germination capabilities, cleaned, disinfected, disinfestated, primed, enhanced, pelleted, encrusted, pilled or coated and may be capable of germinating or may be non-germinating and even deliberately be inactivated by, e.g., irradiation or heating. "Plant" as used herein, includes gymnosperms and angiosperms, monocotyledons and dicotyledons, trees, fruit trees, field and vegetable crops and ornamental species.

A "seed-binding protein" as used herein, means the whole or part of a proteinaceous (protein, protein-like or protein-containing) molecule that is capable of binding using specific intermolecular interactions to a target molecule on the seed, preferably on the seed surface. A seed-binding protein can be a naturally occurring molecule, it can be derived from a naturally occurring molecule, or it can be entirely artificially designed. Binding of the seed-binding protein to the target molecule on the seed preferably occurs with high affinity. The term "affinity," as used herein, refers to the degree to which a seed-binding protein binds to its target molecule so as to shift the equilibrium of target molecule and seed-binding protein towards the presence of a complex formed by their binding. The dissociation constant is commonly used to describe the affinity between a seed-binding protein and its target molecule. Typically, the dissociation constant of the binding between the seed-binding protein and its target molecule on the seed is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M. Binding of the seed-binding protein to the target molecule on the seed is preferably specific. "Specific" as used herein, means that the seed-binding protein preferentially binds to a particular target molecule that is present in a homogeneous or heterogeneous mixture of different molecules. Specificity can also be expressed as the difference in affinity of a seed-binding protein for its target molecule versus the affinity for an unrelated molecule. Preferably, the ratio of the affinity of the seed-binding protein for its target molecule versus its affinity for an unrelated molecule is larger than 10, more preferably, the ratio is larger than 100, most preferably, the ratio is larger than 1000.

A "composition for seed treatment," as used herein, means a composition that is applied to one individual seed or to many seeds simultaneously and that is intended to control seed germination or to influence the germination rate, to protect the germinating seed and/or the emergent plant from attacks by pests or diseases, to protect the germinating seed and/or the emergent plant from damage caused by weeds or other undesired plants, to enhance the vigor, growth and/or establishment of the seedlings and emergent plants, to enhance the yield of the emergent crop, to influence water uptake and/or water retention by seeds and/or seedlings, and/or it may be intended to improve seed handling by smoothening the seed surface, or to protect seeds from damage during storage or handling or by producing seeds of more or less equal size to facilitate sowing.

Compositions for seed treatment should bind strongly to the seed, to avoid their abrasion during application to the seed and/or during seed handling and to avoid dusting during sowing and to avoid wash-off of the composition once the seed is planted or sown in the soil or another substrate for propagation. On the other hand, compositions for seed treatment should not be sticky in order not to cause conglomeration of the treated seeds, and/or not to result in sticking of the seeds to the wall of storage containers or to operator equipment used either during seed treatment or during sowing or planting. Seed-binding proteins hereof bind to seed with high affinity and specificity and, therefore, are particularly useful ingredients in compositions for seed treatment. The composition for seed treatment hereof comprises at least one, preferably, at least two, more preferably, more than two seed-binding protein molecules hereof. One or more seed-binding protein molecules may form a targeting agent as defined later. Preferably, the targeting agent is a combination of two or more seed-binding protein molecules.

In one embodiment, the composition for seed treatment further comprises at least one plant-enhancing agent. A "plant-enhancing agent," as used herein, means one or more active substances intended to positively influence seed germination, plant emergence, plant growth, plant development and/or plant yield including, but not limited to, agrochemical active substances as further defined, disinfectants, disinfestation agents, micro-organisms (such as nitrogen-fixing *Rhizobium* or *Azospirillium* bacteria), plant growth regulators (such as giberillic acid), (micro)nutrients (such as potassium nitrate), plant hormones (such as auxin), minerals, germination stimulants, humectants, stress protectors, or plant inducers (such as Nod factors), or any possible combination of the foregoing. A plant-enhancing agent may occur in any type of formulation, preferred formulations are powders, wettable powders, emulsions, emulsifiable concentrates, dusts, extruder granules, suspensions, suspension concentrates, capsule suspensions or flowable concentrates. The person skilled in the art will understand that it may be advantageous to combine more than one plant-enhancing agent, for example, a composition for seed treatment may contain a combination of one or more fungicides with one or more insecticides, or a combination of one or more nematicides with one or more fertilizers, and so on. The advantage of combining several plant-enhancing agents may be in the broader spectrum of control of pests and/or diseases, and/or by the synergistic action of more than one plant-enhancing agent. In one embodiment, the plant-enhancing agent is used in the composition for seed treatment such that the concentration of the plant-enhancing agent does not inhibit seed germination and is little, preferably not, phytotoxic to the germinating seed or the growing seedling. Preferably, the relative concentration of the plant-enhancing agent versus the total weight of treated seed is in the range of 0.00001-20%, more preferably, in the range of 0.0001-10%, even more preferably, in the range of 0.0005-2%, most preferably, in the range of 0.001-1%.

The composition for seed treatment hereof may further comprise:
  Wetting and dispersing additives, such as polyacrylates, polyurethanes, etc.
  Thickeners, such as natural gums (xanthan gum, gum Arabic, gun ghatti, etc.) agar, alginate, chitin, pectin, etc.
  Coloring agents and effect pigments, such as dyes, brighteners and pigments, including pearlescent pigments.
  Anti-foaming agents, such as polyethylene glycol, glycerine, mineral oil defoamers, silicone defoamers, etc.
  Adhesives, such as alkyleneoxide random and block copolymers, polyvinylacetate, polyvinylalcohol, polyethylene glycols, gelatin, methyl cellulose, paraffin wax, bees wax, etc.
  Solid carriers, such as kaolin, talc, diatomite, calcite, etc.
  Solvents, such as water, aromatic hydrocarbons (e.g., xylene, naphthalene), aliphatic hydrocarbons, alcohols, vegetable oils, etc.

Depending on the type of seed the composition for seed treatment is intended for, the conditions under which it is to be stored and handled, the soil characteristics and the weather conditions under which the seed is expected to germinate and grow, one or more of the following further additives may be added to the composition for seed treatment including, but not limited- to, UV protectants, anti-freezing agents, preservatives, biological control agents or biocides, surfactants, extenders, sequestering agents, plasticizers, phospholipids, flowing agents, coalescing agents, waxes and/or fillers (such as clay, talc, glass fiber, cellulose, pulverized wood, etc.).

The composition for seed treatment as described above may, for example, be maintained as a wettable powder, wettable granule, emulsifiable concentrate, suspension concentrate, microemulsion, capsule suspension, dry microcapsule, tablet or gel or be suspended, dispersed, emulsified or otherwise brought in a suitable liquid medium (such as water or another suitable aqueous, organic or oily medium) so as to provide a (concentrated) liquid composition hereof that has a stability that allows the composition hereof to be suitably stored or (where necessary after further dilution) applied to the seeds. Preferably, the composition for seed treatment is in the form of a wettable powder or—water-dispersible granules, a flowable solution, an emulsion or emulsion concentrate, a suspension or suspension concentrate or a capsule suspension or capsule suspension concentrate. Preferably, the composition for seed treatment hereof can be transported and/or stored prior to final use, optionally (and usually preferably) as a suitable liquid concentrate, dry powder, tablet, capsule suspension, slurry or "wet cake," which can be suitably diluted, dispersed, suspended, emulsified or otherwise suitably reconstituted in a suitable solvent, preferably water, prior to application to the seed. The composition for seed treatment provides for application to the seed using any suitable or desired manual or mechanical technique such as spraying, pouring, immersing, soaking, dressing, coating, encrusting, pelleting, or any other suitable technique.

In one preferred embodiment, the seed-binding proteins present in the composition for seed treatment hereof are capable of binding the plant-enhancing agent or combination of plant-enhancing agents present in the composition hereof onto the seed. "Capable of binding a plant-enhancing agent onto a plant seed," as used herein, means that the seed-binding protein binds in such a way to the plant seed that it can make the plant-enhancing agent adhere firmly to the plant seed, while not making the plant-enhancing agent stick to a storage recipient, to application equipment or to sowing equipment. In order to be capable to bind a plant-enhancing agent onto a plant seed, either one single or multiple seed-binding proteins, whether or not comprised in a targeting agent as further defined, are coupled to the plant-enhancing agent, either by a covalent bond, by hydrogen bonds, by dipole-dipole interactions, by weak Van der Waals forces or by any combination of the foregoing, resulting in the binding of the one or more seed-binding proteins coupled to the plant-enhancing agent to the plant seed.

When binding the plant-enhancing agent or combination of plant-enhancing agents specifically to the seed, the seed-binding protein or seed-binding proteins reduce abrasion and dusting-off of the composition for seed treatment of the treated seeds and/or reduce the stickiness of the treated seeds and, therefore, reduces the chances for seed agglomeration or stickiness to the wall of storage containers or of seed handling or planting or sowing equipment. Preferably, the seed-binding protein or seed-binding proteins present in the composition for seed treatment hereof do not induce germination of the plant seed, nor do they delay or inhibit germination of the plant seed. Preferably, the seed-binding protein or seed-binding proteins present in the composition for seed treatment hereof are not phytotoxic, meaning that they do not interfere with the sprouting or development of the seedling or emergent plant.

In another embodiment, the seed-binding protein is capable of binding a carrier onto a plant seed. A "carrier," as used herein, means any solid, semi-solid or liquid carrier in or on(to) which a substance can be suitably incorporated, included, immobilized, adsorbed, absorbed, bound, encapsulated, embedded, attached, or comprised. In a specific embodiment, the plant seed can be entirely enveloped by a carrier. Non-limiting examples of such carriers include nanocapsules, microcapsules, nanospheres, microspheres, nanoparticles, microparticles, liposomes, vesicles, beads, a gel, weak ionic resin particles, liposomes, cochleate delivery vehicles, small granules, granulates, nano-tubes, bucky-balls, water droplets that are part of a water-in-oil emulsion, oil droplets that are part of an oil-in-water emulsion, organic materials such as cork, wood or other plant-derived materials (e.g., in the form of seed shells, wood chips, pulp, spheres, beads, sheets or any other suitable form), paper or cardboard, inorganic materials such as talc, clay, microcrystalline cellulose, silica, alumina, silicates and zeolites, or even microbial cells (such as yeast cells) or suitable fractions or fragments thereof. "Capable of binding a carrier onto a plant seed," as used herein, means that the binding of the seed-binding protein to the plant seed is strong enough to bind, more preferably to retain, a carrier to the plant seed; depending on the size of the carrier and on the affinity of the seed-binding protein, one or more seed-binding proteins may bind to one or more molecules present at the plant seed and cooperate such that the resulting avidity of the seed-binding proteins for the binding site(s) ensures strong binding of the carrier, preferably retaining the carrier, onto the plant seed. "Retain," as used herein, means that the binding force resulting from the affinity or avidity of either one single seed-binding protein or a combination of two or more seed-binding proteins for its or their target molecule is larger than the combined force and torque imposed by the gravity of the carrier and the force and torque, if any, imposed by shear forces caused by one or more external factors. In one embodiment, the external factor is abrasion occurring during seed treatment or seed handling. One particular advantage of binding a carrier by specific binding over aspecific binding is that specific binding is more resistant to external shear forces applied to the carrier (Cozens-Roberts et al., 1990). Preferably, "retaining" can be evaluated by the fact that the contact between the carrier and the seed is better (expressed in duration of contact, number of carriers per seed, or distance between the carrier and the seed) for a carrier with an antigen-binding protein, compared with a carrier without the antigen-binding protein, when applied under identical conditions. In one preferred embodiment, the carrier bound onto the plant seed by means of one or more seed-binding proteins, will remain bound for a longer period to the plant seed than the same carrier without the seed-binding protein(s).

Preferably, the plant-enhancing agent or combination of plant-enhancing agents as defined above, is comprised in a carrier. Preferably, the carrier is a microcarrier. A "microcarrier," as used herein, is a particulate carrier where the particles are less than 500 μm in diameter, preferably, less than 250 μm, even more preferably, less than 100 μm, most preferably, less than 50 μm. As used herein, "microcarrier," "microparticle," "microsphere," "microcapsule," "nanoparticle," "nanocapsule" and "nanosphere" can be used interchangeably. Microcarriers for delivery of agrochemical active substances (as defined hereinafter) have been described, amongst others, in U.S. Pat. No. 6,180,141, WO 2004/004453, WO 2005/102045 and U.S. Pat. No. 7,494,526, incorporated herein by reference. Characteristics of microcarriers can be such that they enable slow release of the agrochemical active substance, delayed release of the agrochemical or immediate release of the agrochemical, all types of microcarriers have their specific use. Microcarriers may naturally comprise cross-linkable residues suitable for covalent attachment or microcarriers may be derivatized to introduce suitable cross-linkable groups to methods well known in the art. Such derivatization may occur prior to manufacturing of the microcarrier, i.e., at the level of the raw materials that will be used in the manufacturing process, it may occur during the manufacturing process of the microcarrier or it may occur subsequent to the manufacturing of the microcarrier. In one specific embodiment, functional groups on the microcarrier may be bound to a linking agent or spacer, which is on its turn bound to a seed-binding protein as defined above.

Preferably, the seed-binding protein is coupled to the plant-enhancing agent or to the carrier. "Coupled," as used herein, can be any coupling allowing the retention of the plant-enhancing agent or carrier containing the plant-enhancing agent by the seed-binding protein; it can be a covalent as well as a non-covalent binding by hydrogen bonds, by dipole-dipole interactions, by weak Van der Waals forces or by any combination of the foregoing. Preferably, the coupling is a covalent binding. It is clear to the person skilled in the art how seed-binding proteins can be coupled to any type of functional groups present at the outer surface of a carrier. "Functional group," as used herein, means any chemical group to which a protein can be covalently bound, including but not limited to, carboxyl-, amine-, hydroxyl-, sulfhydryl-, or alkyn-group. As a non-limiting example, coupling by forming of a carbodiimide bond between carboxyl groups on the outer surface of the carrier and the amine-groups of the seed-binding protein can be applied. Seed-binding proteins can be coupled with or without linking agents to the carrier. In the case of a microbial cell or phage, the seed-binding protein hereof may be encoded by the microbial cell or phage genome, whereas the plant-enhancing agent is contained in or coupled to the microbial cell or phage, either as a fusion protein or by chemical linking. A "linking agent," as used here, may be any linking agent known to the person skilled in the art; preferably, the linking agent is increasing the flexibility of the seed-binding protein(s), whether or not comprised in a targeting agent (as further defined) bound on the carrier, thereby facilitating the binding of the seed-binding protein(s) to the plant seed. Examples of such linking agents can be found in WO 0024884 and WO 0140310.

When binding the carrier comprising a plant-enhancing agent or a combination of plant-enhancing agents specifically to the seed, the seed-binding protein or seed-binding proteins preferably reduce abrasion and dusting-off of the composition for seed treatment of the treated seeds and, therefore, reduce the losses of plant-enhancing agents comprised in the carrier.

Preferably, the seed-binding protein hereof is an antigen-binding protein. An "antigen-binding protein" as used herein, means the whole or part of a proteinaceous (protein, protein-like or protein-containing) molecule that is capable of binding using specific intermolecular interactions to a target molecule. An "antigen" as used herein is a molecule capable of eliciting an immune response in an animal. An antigen-binding protein can be immunoglobulin-based or it can be based on domains present in proteins including, but not limited to, microbial proteins, protease inhibitors, toxins, fibronectin, lipocalins, single chain antiparallel coiled coil proteins or repeat motif proteins. Non-limiting examples of such antigen-binding proteins are carbohydrate antigen-binding proteins (CBD) (Blake et al., 2006), heavy chain antibodies (hcAb), single domain antibodies (sdAb), minibodies (Tramontano et al., 1994), the variable domain of camelid heavy chain antibodies (VHH), the variable domain of the new antigen receptors (VNAR), affibodies (Nygren et al., 2008), alphabodies (WO 2010/066740), designed ankyrin-repeat domains (DARPins) (Stumpp et al., 2008), anticalins (Skerra et al., 2008), knottins (Kolmar et al., 2008) and engineered CH2 domains (nanoantibodies; Dimitrov, 2009). Preferably, the antigen-binding protein consists of a single polypeptide chain and is not post-translationally modified. More preferably, the antigen-binding protein is derived from an innate or adaptive immune system. Still more preferably, the antigen-binding protein is derived from an immunoglobulin. Most preferably, the antigen-binding protein comprises four framework regions and three complementarity-determining regions, or any suitable fragment thereof (which will then usually contain at least some of the amino acid residues that form at least one of the complementarity-determining regions). Preferably, an antigen-binding protein is easy to produce at high yield, preferably, in a microbial recombinant expression system, and convenient to isolate and/or purify subsequently. Also preferably, an antigen-binding protein is stable, both during storage and during utilization, meaning that the integrity of the antigen-binding protein is maintained under storage and/or utilization conditions, or regained after storage and/or utilization conditions, which may include elevated temperatures, freeze-thaw cycles, changes in pH or in ionic strength, UV-irradiation, presence of harmful chemicals and the like. More preferably, the antigen-binding protein is stable in an agrochemical formulation as defined below. Most preferably, the antigen-binding protein remains stable in an agrochemical formulation (as further defined) when stored at ambient temperature for a period of up to two years or when stored at 54° C. for a period of at least two weeks. Preferably, the antigen-binding protein is selected from the group consisting of DARPins, knottins, alphabodies and VHH. More preferably, the antigen-binding protein is selected from the group consisting of alphabodies and VHH. Most preferably, the antigen-binding protein is a VHH.

Binding of the antigen-binding protein to a target molecule on a plant seed occurs with high affinity: typically, the dissociation constant of the binding between the antigen-binding protein and the target molecule on the seed is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M. Preferably, binding of the antigen-binding protein to its target molecule on the seed site is specific, meaning that the antigen-binding protein preferentially binds to a particular antigen that is present in a homogeneous or heterogeneous mixture of different antigens. Specificity of binding of an antigen-binding protein can be analyzed by methods such as ELISA, as described in Example 2, in which the binding of the antigen-binding protein to its target molecule is compared with the binding of the antigen-binding protein to an unrelated molecule and with aspecific sticking of the antigen-binding protein to the reaction vessel. In certain embodiments, a specific binding interaction will discriminate between desirable and undesirable antigens in a sample, in some embodiments more than about ten- to 100-fold or more (e.g., more than about 1000- or 10,000-fold). Binding of the antigen-binding protein can be specific for seeds of one particular plant species, meaning that the target molecule, present in or on seeds of such plant species, is not or to a much lesser extent present in or on seeds of other plant species; or the binding can be more general to seeds of more than one plant species, if the target molecule is present in or on seeds of more than one plant species. Binding of the antigen-binding protein can be specific for a particular part or side of the plant seed, meaning that the target molecule, present in or on such part or side of the plant seed, is not or to a much lesser extent present on other parts or sides of the plant seed, or the binding can be more general to the whole of the plant seed, if the binding site is present on the entire plant seed.

Preferably, the binding of the antigen-binding protein to the binding site is still functional under harsh conditions, such as low or high temperature, low or high pH, low or high ionic strength, UV-irradiation, low moisture content, low water potential, presence of denaturing chemicals or the like. In one preferred embodiment, the harsh conditions are defined by a pH range from 4 to 9, more preferably, by a pH range from 3 to 10, even more preferably, by a pH range from 2 to 10, most preferably, by a pH range from 1 to 11. In another embodiment, the harsh conditions are defined by a temperature range from 4-50° C., more preferably, a temperature range from 0-55° C., even more preferably, a temperature range from 0-60° C. In another embodiment, the harsh conditions are defined by a moisture content below 50%, preferably, a moisture content below 40%, more preferably, a moisture content below 30%, even more preferably, a moisture content below 25%, most preferably, a moisture content below 20%. In yet another embodiment, the harsh conditions are defined by a water potential below −0.5 MPa, preferably, a water potential below −0.75 MPa, more preferably, a water potential below −1 MPa, even more preferably, a water potential below −1.5 MPa, most preferably, a water potential below −2 MPa. In still another embodiment, the harsh conditions are defined as conditions prevalent in methods for seed treatment as further defined.

Preferably, the binding to the plant seed of the seed-binding protein, preferably, the antigen-binding protein present in the composition for seed treatment, does not interfere with germination of the seed, i.e., the binding of the antigen-binding protein to the plant seed does not induce germination of the seed, neither does it cause delay or inhibition of germination of the plant seed. Preferably, the binding of the antigen-binding protein to the plant seed is not phytotoxic, meaning that the binding of the antigen-binding protein to the plant seed does not negatively interfere with healthy sprouting and development of the seed, seedling or emergent plant.

In one preferred embodiment, the seed-binding protein, preferably, the antigen-binding protein present in the composition for seed treatment hereof, binds to a plant cell wall component. A "plant cell wall component," as used herein, means any molecule as it occurs in the middle lamella, primary or secondary cell wall of higher plants and contributes to the structure of the plant cell wall. The middle lamella is shared by neighboring cells and cements them firmly together; the middle lamella is rich in pectin. The main chemical components of the primary plant cell wall include cellulose. In addition, the primary cell wall contains two groups of branched polysaccharides, the pectins and cross-linking glycans.

Organized into a network with the cellulose microfibrils, the cross-linking glycans increase the tensile strength of the cellulose, whereas the coextensive network of pectins provides the cell wall with the ability to resist compression. Besides these networks, a small amount of protein can be found in all plant primary cell walls. The secondary plant cell wall, which is often deposited inside the primary cell wall as a cell matures, sometimes has a composition nearly identical to that of the earlier-developed primary wall. More commonly, however, additional substances, especially lignin, are found in the secondary cell wall. Besides lignin, cutin, suberin, and other waxy materials are sometimes found in plant cell walls. Preferably, the seed-binding protein, more preferably, the antigen-binding protein present in the composition for seed treatment hereof binds to a plant cell wall component chosen from the group consisting of cellulose, hemicellulose, pectic polysaccharides, proteins, lignin, suberin, cutin or wax. More preferably, the seed-binding protein, more preferably, the antigen-binding protein, present in the composition for seed treatment hereof binds to a plant cell wall component chosen from the group consisting of hemicellulose, pectic polysaccharides, lignin, suberin or cutin. Most preferably, the seed-binding protein, more preferably, the antigen-binding protein present in the composition for seed treatment hereof, binds to a pectic polysaccharide.

Preferably, the seed-binding protein, more preferably, the antigen-binding protein present in the composition for seed treatment hereof, binds to a polysaccharide. "Polysaccharides" as used herein are polymeric carbohydrate structures, formed of repeating units of monosaccharides, joined together by glycosidic bonds, including homopolysaccharides and heteropolysaccharides, but excluding mixed structures with non-carbohydrate units such as glycoproteins and lipoproteins. Preferably, the polysaccharides are not contaminated with other compounds, and have a purity of at least 85% w/w, preferably, 90% w/w, more preferably, 95% w/w, even more preferably, 98% w/w, most preferably, 99% w/w. More than one type of monosaccharide can be present in a polysaccharide. In some cases, the repeating unit may contain slight modifications. Homopolysaccharides are polysaccharides where all repeating units are the same type of monosaccharide; when more than one monosaccharide is present, the polysaccharide is classified as heteropolysaccharide. The structures can be linear or branched, up to structures with a high complexity. Preferably, the seed-binding protein, more preferably, the antigen-binding protein present in the composition for seed treatment hereof, binds to a heteropolysaccharide.

Polysaccharides are distinct from oligosaccharides by their size, complexity and degree of polymerization. "Polysaccharides," as used herein, comprise at least ten monosaccharide units, preferably, at least 15 monosaccharide units. Preferably, the polysaccharide is a structural polysaccharide. Structural polysaccharides are known to the person skilled in the art; structural polysaccharides play a role in the rigidity of an organism, or a part thereof and include, but are not limited to, cellulose, glucan, xylan and pectin. In one preferred embodiment, the structural polysaccharide is derived from a plant.

"Binding to a polysaccharide" as used herein means that the seed-binding protein, preferably, the antigen-binding protein present in the composition for seed treatment hereof, binds a polysaccharide structure, preferably, without cross-reaction with oligosaccharides, as can be measured using a carbohydrate microarray comprising polysaccharides, and related oligosaccharides (Øbro et al., 2009).

In a further preferred embodiment, the seed-binding protein, more preferably, the antigen-binding protein present in the composition for seed treatment hereof, is binding pectin, most preferably, the pectin comprises a low esterified homogalacturonan. Pectin comprises a heterogeneous group of complex polysaccharides, sharing the presence of α-(1-4) linked D-galacturonic acid in the backbone, but further differing in composition, linkage and intermolecular bonds. Normally, three types of pectic polysaccharides are distinguished: (1) homogalacturonan (HG), consisting of linear chains of α-(1-4) linked D-galacturonic acid, (2) rhamnogalacturonan I (RG-I) comprising the repeating unit-4)-α-D-galacturonic acid-(1,2)-α-L-rhamnose-(1- and (3) rhamnogalacturonan II (RG-II) with a highly branched D-galacturonic acid backbone. Some of the carboxyl groups of the galacturonic residues are esterified, mainly as methylester; the degree of esterification may vary from 0-90%. Pectin in which less than 50% of the carboxyl groups are esterified, is normally classified as "low esterified." The degree of esterification determines strongly the physical and chemical properties of pectin.

In still another embodiment, the seed-binding protein, more preferably, the antigen-binding protein, present in the composition for seed treatment hereof, comprises four framework regions and three complementarity-determining regions, or any suitable fragment thereof (which will then usually contain at least some of the amino acid residues that form at least one of the complementarity-determining regions). More preferably, the seed-binding protein, more preferably, the antigen-binding protein present in the composition for seed treatment hereof, is derived from a heavy chain camelid antibody, even more preferably, the antigen-binding protein comprises a VHH sequence. Heavy chain camelid antibodies, and the VHH-derived sequences are known to the person skilled in the art. Camelid antibodies have been described, amongst others in WO 9404678 and in WO 2007/118670, incorporated herein by reference. Most preferably, the VHH consists of a sequence selected from the group consisting of SEQ ID NO:1-SEQ ID NO:11 (VHH 6B5, 6D7, 6D11, 6F2, 6H4, 7A5, 7A7, 7E9, 8A4, 8D6, and 12C3), or any suitable fragment thereof (which will then usually contain at least some of the amino acid residues that form at least one of the complementarity-determining regions) or homologues thereof. "Homologues," as used herein, are sequences wherein each or any framework region and each or any complementarity-determining region shows at least 80% identity, preferably, at least 85% identity, more preferably, 90% identity, even more preferably, 95% identity with the corresponding region in the reference sequence (i.e., FR1 homologue versus FR1_reference, CDR1_homologue versus CDR1_reference, FR2_homologue versus FR2_reference, CDR2_homologue versus CDR2_reference, FR3_homologue versus FR3_reference, CDR3_homologue versus CDR3_reference and FR4_homologue versus FR4_reference) as measured in a BLASTp alignment (Altschul et al., 1997; FR and CDR definitions according to Kabat).

In still another embodiment, the plant seed is a seed of a crop. "Crop" or a "cash crop" as used herein means a plant species or variety that is grown to be harvested as food, livestock fodder, fuel raw material, or for any other economic purpose. As a non-limiting example, the crops can be maize, cereals, such as wheat, rye, barley and oats, sorghum, rice, sugar beet and fodder beet, fruit, such as pome fruit (e.g., apples and pears), citrus fruit (e.g., oranges, lemons, limes, grapefruit, or mandarins), stone fruit (e.g., peaches, nectarines or plums), nuts (e.g., almonds or walnuts), soft fruit (e.g., cherries, strawberries, blackberries or raspberries), the plantain family or grapevines, leguminous crops, such as beans, lentils, peas and soya, oil crops, such as sunflower, safflower, rapeseed, canola, castor or olives, cucurbits, such as cucumbers, melons or pumpkins, fiber plants, such as cotton, flax or hemp, fuel crops, such as sugarcane, miscanthus or switchgrass, vegetables, such as potatoes, tomatoes, peppers, lettuce, spinach, onions, carrots, egg-plants, asparagus or cabbage, ornamentals, such as flowers (e.g., petunias, pelargoniums, roses, tulips, lilies, or chrysanthemums), shrubs, broad-leaved trees (e.g., poplars or willows) and evergreens (e.g., conifers), grasses, such as lawn, turf or forage grass or other useful plants, such as coffee, tea, tobacco, hops, pepper, rubber or latex plants. Preferably, the crop is selected from the group consisting of maize, wheat, sorghum, rye, soybean, rice, cotton, canola, sunflower, sugar beet, potatoes, vegetables, flowers, turf and forage grass.

Also described is a method for manufacturing a composition for seed treatment hereof, the method comprising (i) selecting at least one seed-binding protein hereof, preferably, more seed-binding proteins hereof, whether or not comprised in a targeting agent as further defined, and (ii) coupling the seed-binding protein(s) to a plant-enhancing agent or a combination of plant-enhancing agents, and optionally (iii) adding further components that may be suitable for compositions for seed treatment (such as wetting and dispersing additives, thickeners, coloring agents, anti-foaming agents, adhesives, solid carriers and/or solvents) as above described. Preferably, the plant-enhancing agent is comprised in a carrier, more preferably, the seed-binding protein(s) are coupled to the carrier comprising the plant-enhancing agent.

A second aspect hereof is a method for treating a plant seed, the method comprising (1) preparing a composition for seed treatment hereof and (2) applying the composition to the seed.

Methods for applying a composition for seed treatment to a seed are known to the person skilled in the art and include, but are not limited to, seed dressing, seed soaking, seed coating, film coating, multilayer coating, encrusting, pilling, pelleting, or any combination of the foregoing. The method for treating a seed hereof involves applying to one individual seed or to more seeds simultaneously a composition for seed treatment hereof using any of the methods for seed treatment as described above. The composition for seed treatment hereof may be used as such, or may first be diluted into a suitable solvent, preferably water, before being applied to one or more seeds. The composition hereof can be sprayed, dripped, or poured onto the seeds or seeds may be soaked or immersed into a composition for seed treatment using suitable equipment and techniques including, but not limited to, drum coaters, fluidized bed techniques, rotary coaters, rotastatic seed treaters, roller mill methods, side vended pans, tumble mixers, spouted beds and the like. Seeds may be treated as they had been harvested, but seeds may also receive any kind of pre-treatment before being treated with a composition for seed treatment. Suitable pre-treatments include, but are not limited to, cleaning, sorting of the seeds by size, weight, density or by germination potency, disinfection or disinfestation of the seeds, and/or priming or pre-germination of the seeds, by methods such as soaking the seeds in water and drying them again or by osmo-conditioning or other suitable methods. Seeds may be treated at any time between harvesting and sowing or planting of the seed. Usually, seeds are treated prior to sowing or planting of the seeds with a composition for seed treatment and are dried after treatment to enable storage for prolonged periods. Alternatively, seeds may be treated immediately before sowing or planting, e.g., a seed dressing may be applied to cereal seeds immediately prior to proceeding to seeding, or a composition for seed treatment may be applied to rice seeds at the time they are pre-soaked in water before being sown in the paddies. Still otherwise, a composition for seed treatment can be applied to the seeds or to the immediate vicinity of the seeds simultaneous with the sowing or planting, and special devices and methods, such as the ones described in WO 98/25445 and WO 2006/112700, may be utilized to do so.

Preferably, the method for treating the seeds is such that it doesn't damage the seeds, nor degrades or inactivates the agrochemical active substance or plant-enhancing agent comprised therein. In another embodiment, the method for treating the seeds is such that it doesn't induce germination of the seeds, nor delays or inhibits germination of the seeds. Preferably, the method for treating the seeds is such that it results in an even distribution of the composition for seed treatment on the seeds or, alternatively, that it results in a very specific distribution of the composition for seed treatment over the seed surface, e.g., predominantly at the site of germination of the seed. Even more preferably, the method is such that it allows binding of the seed-binding protein(s), more preferably, the antigen-binding protein(s) present in the composition for seed treatment to bind to the seeds.

A third aspect hereof is a plant seed treated with a composition comprising at least one antigen-binding protein comprising an amino acid sequence that comprises four framework regions and three complementarity-determining regions or any suitable fragment thereof (which will then usually contain at least some of the amino acid residues that form at least one of the complementarity-determining regions).

The antigen-binding protein comprising an amino acid sequence that comprises four framework regions and three complementarity-determining regions or any suitable fragment thereof preferably binds specifically to the plant seed, more preferably, in doing so, it is capable to bind a plant-enhancing agent or a combination of plant-enhancing agents (as defined earlier), whether or not comprised in a carrier, to a plant seed. However, it is also envisaged that the antigen-binding protein comprising an amino acid sequence that comprises four framework regions and three complementarity-determining regions or any suitable fragment thereof, which is comprised in the composition for seed treatment, may as well act as an agrochemical active substance (as further defined) in itself. Indeed, an amino acid sequence that comprises four framework regions and three complementarity-determining regions or any suitable fragment thereof, may have an antifungal (e.g., by interfering with fungal growth), insecticidal or nematicidal (e.g., by inhibiting activity of crucial digestive enzymes) by itself as non-limiting examples.

Preferably, the composition for seed treatment, comprising at least one antigen-binding protein comprising an amino acid sequence that comprises four framework regions and three complementarity-determining regions or any suitable fragment thereof is a composition hereof. More preferably, the antigen-binding protein is derived from a heavy chain camelid antibody, even more preferably, the antigen-binding protein comprises a VHH sequence, most preferably, the antigen-binding protein is a VHH selected from the group consisting of SEQ ID NO:1-SEQ ID NO:11, or any suitable fragment thereof (which will then usually contain at least some of the amino acid residues that form at least one of the complementarity-determining regions) or homologues thereof.

Treating of the plant seed with a composition hereof may occur at any time prior to, immediately before or during sowing of the seed, using any of the methods described before.

In one embodiment, a seed so treated with a composition hereof and/or the seedling emerging from the treated seed and/or a seed sown in the immediate vicinity of the seed so treated with a composition hereof, and/or the seedling emerging from the seed sown in the immediate vicinity of the seed so treated with a composition hereof is protected from seed-borne pathogens and/or soil-borne pathogens. "Seed-borne pathogens" as used herein mean pathogens that cause plant disease via a biological object (e.g., spore, mycelium, sclerotium, cells) that is able to infect the host and that is carried with, on the surface of or within the plant seed. Examples of seed-borne pathogens include fungi (e.g., *Tilletia tritici, Ustilago nuda*), bacteria (e.g., *Pseudomonas syringae*), or viruses (e.g., lettuce mosaic virus). "Soil-borne pathogens" as used herein means pathogens that cause plant disease via a biological object (e.g., spore, mycelium, sclerotium, cells) that is able to infect the host and that comes to the plant by way of the soil. Examples of soil-borne pathogens include fungi (e.g., *Rhizoctonia solani*), bacteria (e.g., *Erwinia*), viruses (e.g., lettuce necrotic stunt virus) and nematodes (e.g., *Meloidogyne*). "Protected from seed-borne and/or soil-borne pathogens," as used herein, means that the treated seed or the seedling emerging from the treated seed are not, or to a much lesser extent, affected by seed-borne and/or soil-borne pathogens compared to seeds or seedlings emerging therefrom to which the composition hereof was not applied. "Immediate vicinity," as used herein, means within a distance of 10 cm or less from the treated seed, preferably, within a distance of 5 cm or less from the treated seed, more preferably, within a distance of 2 cm or less from the treated seed, most preferably, within a distance of 1 cm or less from the treated seed.

A seed so treated with a composition hereof will benefit from the high affinity binding to the seed of the seed-binding proteins, preferably the antigen-binding proteins, coupled to the plant-enhancing agent(s), whether or not comprised in a carrier, present in the composition for seed treatment, which may result in prolonged periods of protection of the seeds from seed-borne and/or soil-borne pathogens and/or in reduced amounts of plant-enhancing agent that needs to be present in the composition for seed treatment in order to provide adequate protection of the treated seed from seed-borne and/or soil-borne pathogens in comparison with seeds without application of the composition hereof. Preferably, the plant-enhancing agent is chosen from the group comprised of fungicides, nematicides, insecticides, bactericides or viricides. Examples of suitable agrochemical active substances to treat seed and soil-borne pathogens include, but are not limited to captan, thiram, metalaxyl, fludioxonil, difenoconazole, iprodione, tebuconazole, carboxin, myclobutanil, flutriafol, triadimenol, triticonazole, imizalil, bitertanol, fluoxastrobin, azoxystrobin, pencycuron, triazoxide, mancozeb, and PCNB as fungicides, terbufos, chlorpyrifos, fipronil, chloretoxyfos, tefluthrin, carbofuran, tebupirimifos, imidacloprid, thiomethoxam, cypermethrin, triflumuron, chlorantraniliproles and methiocarb as insecticides, abamectin, thiodicarb and aldoxycarb as nematicides and streptomycin, penicillin, tetracyclin, ampicillin and oxolinic acid as bactericides. Also preferably, the seed is treated with a composition for seed treatment comprising one or a combination of plant-enhancing agents, that are comprised in a composition for slow or delayed release, which is particularly advantageous for autumn-sown seeds, which require prolonged periods of protection against soil-borne pathogens, in particular, against pathogens occurring in winter under the snow deck, such as snow mold affecting rye seeds.

In another embodiment, a seedling emerging from a seed, treated with a composition according to the invention, and/or from a seed sown in the immediate vicinity (as defined above) of the treated seed may be protected from damage caused by plant pests and/or diseases. "Plant pests and/or diseases," as used herein, means pathogens that cause damage to the plant and/or that cause plant disease via a biological object (e.g., spore, mycelium, insect) that is able to infect the host and that comes to the plant by way of the ground surface or the air. Examples of plant pests and/or disease include insects, mites, or snails, fungi, viruses. "Protected from plant pests and/or diseases," as used herein, means that the seedling emerging from the treated seed or from a seed sown in the immediate vicinity, as defined above, of the treated seed are not or to a much lesser extent affected by plant pests and/or diseases compared to seeds or seedlings emerging therefrom to which the composition hereof was not applied.

A seed so treated with a composition hereof will benefit from the high affinity binding to the seed of the seed-binding proteins, preferably the antigen-binding proteins, coupled to the plant-enhancing agent(s), whether or not comprised in a carrier, present in the composition for seed treatment, which may result in prolonged periods of protection of the seedlings from plant pests and/or disease and/or in reduced amounts of plant-enhancing agent that needs to be present in the composition for seed treatment in order to provide adequate protection of the seedling emerging from the treated in comparison with seeds without application of the composition. Preferably, the plant-enhancing agent is chosen from the group comprised of insecticides, miticides, acaricides, molluscicides, fungicides, bactericides or viricides. Examples of suitable agrochemical active substances to protect from damage caused by plant pests and/or disease include, but are not limited to, metalaxyl, fludioxinil, carbendazim, ipconazole, carboxin, thiabendazole, fluquinconazole, carpropamid, fuberidazole, prochloraz, oxadixyl, prothioconazole and thifluzamide as fungicides, imidacloprid, clothianidin, thiomethoxam, thiodicarb and aldoxycarb as insecticides. Also preferably, the seed is treated with a composition for seed treatment comprising one or a combination of plant-enhancing agents that have systemic activity and which is/are taken up by the root system of the seedling and transported upward to the aerial parts of the growing seedling, which may decrease the need to apply foliar-applied agrochemical compositions to the emerging seedlings.

In yet another embodiment, a seed so treated with a composition hereof and/or a seedling emerging from a seed, treated with a composition hereof, and/or from a seed sown in the immediate vicinity (as defined above) of the treated seed may be protected from damage caused by weeds and/or other undesired plants. "Protected from damage caused by weeds and/or other undesired plants," as used herein, means that the treated seed and/or the seedling emerging from the treated seed and/or from a seed sown in the immediate vicinity, as defined above, of the treated seed are not, or to a much lesser extent, affected by damage caused by weeds and/or other undesired plants compared to seeds or seedlings emerging therefrom to which the composition hereof was not applied. Such protection can be direct, in cases where the plant-enhancing agent comprised in the composition for seed treatment, is a herbicide, or it can be indirect, in cases where the plant-enhancing agent comprised in the composition for seed treatment is a safener, in which case the protection of the emergent plant needs to be completed with a foliar application of a herbicide. A "safener," as used herein, is an agrochemical active substance (as further defined) that protects a crop from herbicide damage.

A seed so treated with a composition hereof will benefit from the high affinity binding to the seed of the seed-binding proteins, preferably the antigen-binding proteins, coupled to the plant-enhancing agent(s), whether or not comprised in a carrier, present in the composition for seed treatment, which may result in prolonged periods of protection of the seedlings from damage caused by weeds and/or other undesired plants and/or in reduced amounts of plant-enhancing agent that needs to be present in the composition for seed treatment in order to provide adequate protection of the seedling emerging from the treated seeds in comparison with seeds not treated with a composition hereof. Preferably, the plant-enhancing agent is chosen from the group comprised of herbicides and safeners. Examples of suitable agrochemical active substances to protect from damage caused by weeds and/or other undesired plants include, but are not limited to, triasulfuron and clomazone as herbicides and cloquintocet-methyl, cyometrinil, flurazole, fluxofenim, mefenpyr-diethyl, naphthalic anhydride and oxabetrinil as safeners.

In still another embodiment, a seedling emerging from a seed, treated with a composition for seed treatment hereof, and/or from a seed sown in the immediate vicinity (as defined above) of the treated seed, may have an enhanced yield. "Enhanced yield," as used herein, means an increase in the yield of a harvestable product of the plant by a measurable amount over the yield of the same harvestable product of the plant produced under identical conditions, but without application of the subject method. Preferably, the yield is increased by 1% or more, more preferably, the yield is increased by 1.5% or more, even more preferably, the yield is increased by 2% or more, most preferably, the yield is increased by 2.5% or more. Yield-enhancing compounds are known to the person skilled in the art and include, but are not limited to, plant growth regulators such as auxins, gibberellins, nod-factors and microbes such as *Bacillus subtilis*. However, it is clear for the person skilled in the art that, for instance, fungicides, insecticides, nematicides and herbicides by preventing yield losses will also have a yield-enhancing effect.

A seed treated with a composition hereof will benefit from the high affinity binding to the seed of the plant-enhancing agent present in the composition for seed treatment, which may result in enhanced yields and/or in reduced amounts of plant-enhancing agent that needs to be present in the composition for seed treatment in order to result in measurable enhanced yields in comparison with seeds without application of the composition hereof. Preferably, the plant-enhancing agent is chosen from the group comprised of fertilizers, micro-nutrients, plant growth regulators, stress protectors, humectants, plant inducers, microbial agents or plant hormones.

The plant seed, treated with a composition hereof may be under the form of a dressed seed, a film-coated seed, an encrusted seed, a mini pill, a standard pill, a split-pill or in any other suitable form. Preferably, the treated seed hereof can be stored for prolonged periods of time without losing germination potency or crop yield. Preferably, germination of a plant seed, treated with a composition hereof, is not induced, nor delayed, nor inhibited.

In one embodiment, the plant seed is a seed of a crop, as defined above. More preferably, the plant seed is a seed from a crop, chosen from the group consisting of maize, wheat, sorghum, rye, soybean, rice, cotton, canola, sunflower, sugar beet, potatoes, vegetables, flowers, turf and forage grass.

In another embodiment, the plant seed is a seed of an improved crop. An "improved crop," as used herein, means a crop that is either genetically modified or that is otherwise selected by natural selection, marker-assisted selection or genomic selection or methods of conventional breeding including, but not limited to, (molecular) mutation breeding techniques, to have improved traits over wild-type crops. Examples of improved crops include, but are not limited to, glyphosate-tolerant crops, *Bacillus thuringiensis* toxin-expressing crops, disease-resistant varieties of crops, hybrid crop varieties with enhanced yields, etc.

A fourth aspect hereof is a method comprising the steps of (i) treating a seed with a composition hereof, and (ii) sowing the treated seed, wherein the composition:
 (a) protects the plant seed against seed-borne and/or soil-borne pathogens; and/or
 (b) protects the plant growing from the treated seed and/or in the immediate vicinity of the treated seed against damage caused by pests and/or diseases and/or
 (c) protects the plant seed and/or the plant growing from the treated seed and/or in the immediate vicinity of the treated seed against damage caused by weeds and/or other undesired plants and/or (d) enhances the yield of the plant growing from the treated seed and/or in the immediate vicinity of the treated seed.

Treating plant seeds with a composition for seed treatment hereof and then sowing them, whereby the composition either better protects the so treated seed from seed- and/or soil-borne pathogens, and/or protects the emerging crop from plant pests and/or diseases, and/or protects the seed and/or the emergent plant from damage caused by weeds and/or other undesired plants, and/or results in an enhanced yield, may all contribute to more uniform crop development and harvesting and, therefore, improved crop quality as compared with seeds not treated and sown according to the method hereof described above.

A fifth aspect hereof is a seed-binding protein, wherein the seed-binding protein is an antigen-binding protein comprising an amino acid sequence that comprises four framework regions and three complementarity-determining regions, or any suitable fragment thereof (which will then usually contain at least some of the amino acid residues that form at least one of the complementarity-determining regions).

Preferably, the antigen-binding protein is easy to produce at high yield, preferably in a microbial recombinant expression system, and convenient to isolate and/or purify subsequently. Also preferably, the antigen-binding protein is stable, both during storage and during utilization, meaning that the integrity of the antigen-binding protein is maintained under storage and/or utilization conditions, which may include elevated temperatures, freeze-thaw cycles, changes in pH or in ionic strength, UV-irradiation, presence of harmful chemicals and the like. More preferably, the antigen-binding protein is stable in an agrochemical formulation as defined below. Most preferably, the antigen-binding protein remains stable in an agrochemical formulation (as further defined) when stored at ambient temperature for a period of up to two years or when stored at 54° C. for a period of at least two weeks.

Binding of the antigen-binding protein to a target molecule on a plant seed preferably occurs with high affinity. Typically, the dissociation constant of the binding between the antigen-binding protein and the target molecule on the seed is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M. Preferably, binding of the antigen-binding protein to its target molecule is specific, meaning that the antigen-binding protein preferentially binds to a particular antigen that is present in a homogeneous or heterogeneous mixture of different antigens. Specificity of binding of an antigen-binding protein can be analyzed by methods such as ELISA, as described in Example 2, in which the binding of the antigen-binding protein to its target molecule is compared with the binding of the antigen-binding protein to an unrelated molecule and with aspecific sticking of the antigen-binding protein to the reaction vessel. In certain embodiments, a specific binding interaction will discriminate between desirable and undesirable antigens in a sample, in some embodiments more than about ten- to 100-fold or more (e.g., more than about 1000- or 10.000-fold). Preferably, the binding of the antigen-binding protein to its target molecule is still functional under harsh conditions, such as low or high temperature, low or high pH, low or high ionic strength, UV-irradiation, low moisture content, low water potential, presence of denaturing chemicals or the like. In one preferred embodiment, the harsh conditions are defined by a pH range from 4 to 9, more preferably, by a pH range from 3 to 10, even more preferably, by a pH range from 2 to 10, most preferably, by a pH range from 1 to 11. In another embodiment, the harsh conditions are defined by a temperature range from 4-50° C., more preferably, a temperature range from 0-55° C., even more preferably, a temperature range from 0-60° C. In another embodiment, the harsh conditions are defined by a moisture content below 50%, preferably, a moisture content below 40%, more preferably, a moisture content below 30%, even more preferably, a moisture content below 25%, most preferably, a moisture content below 20%. In yet another embodiment, the harsh conditions are defined by a water potential below −0.5 MPa, preferably, a water potential below −0.75 MPa, more preferably, a water potential below −1 MPa, even more preferably, a water potential below −1.5 MPa, most preferably, a water potential below −2 MPa. In still another embodiment, the harsh conditions are defined as conditions prevalent in methods for seed treatment as above described.

Preferably, the antigen-binding protein is derived from a camelid antibody. More preferably, the antigen-binding protein is comprised in a VHH sequence. Most preferably, the antigen-binding protein is comprised in a VHH sequence, selected from the group consisting of SEQ ID NO:1-SEQ ID NO:11 (VHH 6B5, 6D7, 6D11, 6F2, 6H4, 7A5, 7A7, 7E9, 8A4, 8D6 and 12C3), or any suitable fragment thereof or homologues thereof. Preferably, the antigen-binding protein is binding a plant cell wall component. More preferably, the antigen-binding protein is binding to a plant cell wall component chosen from the group consisting of hemicellulose, pectic polysaccharides, lignin, suberin or cutin. Even more preferably, the antigen-binding protein hereof, binds to a polysaccharide. Preferably, the polysaccharides are not contaminated with other compounds, and have a purity of at least 85% w/w, preferably, 90% w/w, more preferably, 95% w/w, even more preferably, 98% w/w, most preferably, 99% w/w. Preferably, the polysaccharide is a structural polysaccharide and/or a heteropolysaccharide. Even more preferably, the antigen-binding protein hereof is binding pectin, preferably, the pectin comprises a low esterified homogalacturonan.

In one preferred embodiment, the polysaccharide, preferably, the heteropolysaccharide or structural polysaccharide, more preferably, the pectic polysaccharide, is in solution, such as pectin in fruit juice as a non-limiting example. In another embodiment, the polysaccharide, preferably, the heteropolysaccharide or structural polysaccharide, more preferably, the pectic polysaccharide, is comprised in a solid surface, such as a seed surface as a non-limiting example. In still another embodiment, the polysaccharide, preferably, the heteropolysaccharide or structural polysaccharide, more preferably, the pectic polysaccharide, is comprised in vegetable material, such as plant cuttings used for vegetative propagation of a plant, tubers or bulbs.

In still another embodiment, a nucleic acid sequence encoding any of the above antigen-binding proteins or functional fragments thereof is also part of the disclosure. The invention also encompasses the use of any antigen-binding protein hereof to isolate amino acid sequences that are responsible for specific binding to a plant seed, preferably, to a plant cell wall component, more preferably, to a (pectic) polysaccharide, to construct artificial binding domains based on the amino acid sequences. Indeed, in the antigen-binding proteins hereof, the framework regions and the complementarity-determining regions are known, and the study of derivatives of the antigen-binding proteins, also binding to a plant seed, preferably binding to the same plant cell wall component, more preferably, to the same (pectic) polysaccharide, will allow deducing the essential amino acids involved in binding the plant seed, preferably, to a plant cell wall component, more preferably, to (pectic) polysaccharide. This knowledge can be used to construct a minimal antigen-binding protein and to create derivatives thereof.

Further, the disclosure also envisages expression vectors comprising nucleic acid sequences encoding any of the above antigen-binding proteins or functional fragments thereof, as well as host cells expressing such expression vectors. Suitable expression systems include constitutive and inducible expression systems in bacteria or yeasts, virus expression systems, such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris*, and the like. Suitable animal host cells include HEK 293, COS, S2, CHO, NSO, DT40 and the like. The cloning, expression and/or purification of the antigen-binding proteins can be done according to techniques known by the person skilled in the art.

Although naive or synthetic libraries of VHH (for examples of such libraries, see WO 9937681, WO 0043507, WO 0190190, WO 03025020 and WO 03035694) may contain suitable binders to plant seeds, one embodiment hereof includes the immunization of an individual of a species of Camelidae with one or a combination of several plant cell wall components, to expose the immune system of the animal to the plant cell wall components. Thus, as further described herein, such VHH sequences can preferably be generated or obtained by suitably immunizing a species of Camelidae with one or a combination of several plant cell wall components, by obtaining a suitable biological sample from the Camelidae species (such as a blood sample, or any sample of B-cells), and by generating VHH sequences directed against a desired plant cell wall component, starting from the sample. Such techniques will be clear to the skilled person. Yet another technique for obtaining the desired VHH sequences involves suitably immunizing a transgenic mammal that is capable of expressing heavy chain antibodies (i.e., so as to raise an immune response and/or heavy chain antibodies directed against a plant cell wall component), obtaining a suitable biological sample from the transgenic mammal (such as a blood sample, or any sample of B-cells), and then generating VHH sequences directed against the plant cell wall component starting from the sample, using any suitable technique known per se. For example, for this purpose, the heavy chain antibody-expressing mice and the further methods and techniques described in WO 02085945 and in WO 04049794 can be used.

Accordingly, the invention encompasses methods of generating antigen-binding proteins hereof. As a non-limiting example, a method is provided for generating antigen-binding proteins specifically binding to polysaccharides, preferably to pectic polysaccharides comprising:

(i) immunizing an animal with a complex mixture of plant cell wall components, and
(ii) selecting antigen-binding proteins that are binding to polysaccharide-enriched plant extracts; and
(iii) screening for antigen-binding proteins specifically binding to (pectic) polysaccharides.

The screening for antigen-binding proteins, as a non-limiting example, specifically binding to a plant cell wall component may, for example, be performed by screening a set, collection or library of cells that express heavy chain antibodies on their surface (e.g., B-cells obtained from a suitably immunized Camelid), or bacteriophages that display a fusion of genIII and VHH at their surface, by screening of a (naïve or immune) library of VHH sequences, or by screening of a (naïve or immune) library of nucleic acid sequences that encode VHH sequences, which may all be performed in a manner known per se, and which method may optionally further comprise one or more other suitable steps, such as, for example, and without limitation, a step of affinity maturation, a step of expressing the desired amino acid sequence, a step of screening for binding and/or for activity against the desired plant cell wall component, a step of determining the desired amino acid sequence or nucleotide sequence, a step of introducing one or more nucleic acid substitutions, a step of formatting in a suitable multivalent and/or multispecific format, a step of screening for the desired biological and/or physiological properties (i.e., using a suitable assay known in the art), and/or any combination of one or more of such steps, in any suitable order.

A sixth aspect hereof is the use of a seed-binding protein hereof.

In one preferred embodiment, a seed-binding protein, preferably, an antigen-binding protein hereof, most preferably, a VHH selected from the group consisting of SEQ. ID NOS:1-11 or any suitable fragment thereof, is used to bind a plant-enhancing agent to a plant seed. As explained above, the seed-binding protein, preferably, the antigen-binding protein may be coupled to a plant-enhancing agent, or to a carrier comprising a plant-enhancing agent, whereby the seed-binding protein, preferably, the antigen-binding protein is capable of binding, preferably of retaining, the plant-enhancing agent in a specific way to the seed. However, it is clear for the person skilled in the art that the plant seed-binding proteins hereof, especially the polysaccharide antigen-binding proteins, comprising an amino acid sequence that comprises four framework regions and three complementarity-determining regions or any suitable fragment thereof, can be applied for other uses.

In another embodiment, the seed-binding protein, preferably, the antigen-binding protein is used to determine the presence and/or concentration of a polysaccharide in a sample. Methods to determine the presence and/or concentration of a compound, for example, a polysaccharide, using antibodies are known to the person skilled in the art and include, but are not limited to, immunoprecipitation, fluorescent immunoassay, radio immunoassay (RIA), enzyme-linked immunosorbent assay (ELISA) and magnetic immunoassay (MIA). The seed-binding protein, preferably, the antigen-binding protein hereof can be labeled to facilitate the detection and/or quantification of the compound. Labeling of antigen-binding proteins is known to the person skilled in the art, and includes direct labeling and indirect labeling. In direct labeling, the antigen-binding protein itself is labeled by a directly detectable label such as, but not limited to, a color label, a fluorescent label, a radioactive label or a magnetic particle. Fluorescent labels are especially useful, and include, but are not limited to, fluorescein isothiocyanate (FITC) and other fluorescein derivatives, tetramethylrhodamine isothiocyanate (TRITC) and other rhodamine derivatives, R-pycoerythrin fluorescent protein (R-PE) and R-PE:cyanine-5, and allophycocyanin. Alternatively, the labeling can be carried out in an indirect way. In this case, the seed-binding protein, preferably, the antigen-binding protein hereof, can be bound to a detectable secondary compound, or is fused or bound to a tag, which on its own is not directly detectable, but can be detected by binding to a detectable secondary compound. It is obvious for the person skilled in the art that the detection can be the result of a chain of events, such as, but not limited to, serial binding of compounds, or activation of the label after binding.

As used herein, a "sample" is a portion, piece or segment representative for a whole that one wants to analyze for the presence and/or concentration of one or more polysaccharides. The sample can be a part that is withdrawn from the whole, or it can be the whole, measured at a representative point in place and/or time, as is the case for a sample measured on line by a biosensor during fermentation. As a non-limiting example, the sample can be a food sample, wherein the presence or concentration of the polysaccharide needs to be determined or changed in relation to allergenic capacity of the polysaccharide, or in relation to wanted or unwanted physical, chemical or microbiological characteristics of the polysaccharide, changing the quality parameters of the food stuff, such as an altered shelf life. As a non-limiting example, pectin de-esterification plays an important role in fruit softening during ripening (Goulao, 2010), and determination of the pectin structure is essential in understanding the role of the de-esterification in the fruit softening event. Immunoprofiling of pectic polysaccharides, useful, amongst others, during fruit ripening is known to the person skilled in the art and has been described by Willats and Knox (1999). Another example is the use of pectin for increasing the water holding capacity of foodstuff or for the stabilization of fruit juices and milk drinks. In addition, pectin can increase the shelf life of processed meat (Zheng et al., 1999), and pectin is often used as dietary fiber.

In another embodiment, the seed-binding protein, preferably, the antigen-binding protein, is used to isolate a polysaccharide from a sample. Isolation of the polysaccharide may be used to purify the polysaccharide out of a mixture, or it may be intended to remove a contaminating or otherwise undesirable polysaccharide out of a sample. Methods to use antibodies for isolating compounds are known to the person skilled in the art and include, but are not limited to, immunoprecipitation and affinity chromatography. Alternatively, the seed-binding protein, preferably, the antigen-binding protein hereof, may be bound to a membrane, in order to be used in membrane filtration or similar techniques. In a special embodiment, the antigen-binding protein may be fused to a protein of interest that one wants to purify, and the purification is carried out by contacting the mixture with a polysaccharide comprising matrix. Non-limiting examples of the isolation and/or purification can be found in wastewater treatment. Indeed, the wastewater of some fruit processing plants, but especially the wastewater of the coffee industry, is pectin rich, and high in BOD and COD. Purification using chemical coagulation and degradation with radiation has been proposed to reduce the COD (Zayas et al.; 2007). However, this method is rather expensive. Purification using an immunoaffinity process (Harris, 1999) would be an environmentally friendly solution, allowing the recuperation of pectin as valuable side stream. The seed-binding proteins, preferably, the antigen-binding proteins hereof, are especially suited for this purpose, due to their low production cost and their stability in adverse environments.

In a similar way, pectin antigen-binding proteins hereof could be used in the production of pectin. The classical production method consists of an extraction of the raw material (such as citrus peels), a separation from the extracted material, and an alcohol precipitation of the pectin from the juice. The precipitation is non-selective, and yields a mixture of pectins. The use of antigen-binding proteins hereof would allow purification of specific fractions at low cost.

A seventh aspect hereof is an agrochemical composition, comprising at least one seed-binding protein, preferably, an antigen-binding protein hereof.

An "agrochemical composition" as used herein means a composition for agrochemical use, as further defined, comprising at least one agrochemical active substance, as further defined, optionally with one or more additives favoring optimal dispersion, atomization, deposition, leaf wetting, distribution, retention and/or uptake of agrochemicals. As a non-limiting example, such additives are diluents, solvents, adjuvants, surfactants, wetting agents, spreading agents, oils, stickers, thickeners, penetrants, buffering agents, acidifiers, anti-settling agents, anti-freeze agents, photo-protectors, defoaming agents, biocides and/or drift control agents.

"Agrochemical use," as used herein, not only includes the use of agrochemical compositions as defined above that are suitable and/or intended for use in field grown crops (e.g., agriculture), but also includes the use of agrochemical compositions that are meant for use in greenhouse grown crops (e.g., horticulture/floriculture) or hydroponic culture systems or uses in public or private green spaces (e.g., private gardens, parks, sports fields) for protecting plants or parts of plants including, but not limited to, bulbs, tubers, fruits and seeds (e.g., from harmful organisms, diseases or pests), for controlling, preferably, promoting or increasing, the growth of plants; and/or for promoting the yield of plants, or the parts of plants that are harvested (e.g., its fruits, flowers, seeds, etc.) and even the use of agrochemical compositions that are suitable and/or intended for non-plant uses such as household uses (for example, herbicides or insecticides for household use or agents to protect fabrics or wood from damage caused by harmful organisms), or industrial uses (for example, agents to prevent fouling or to protect stored goods from damage by harmful organisms) or uses by pest control operators (for example, to control undesirable insects and rodents etc.).

"Agrochemical active substance," as used herein, means any active substance or principle that may be used for agrochemical use, as defined above. Examples of such agrochemical active substances will be clear to the skilled person and may, for example, include compounds that are active as insecticides (e.g., contact insecticides or systemic insecticides, including insecticides for household use), acaricides, miticides, herbicides (e.g., contact herbicides or systemic herbicides, including herbicides for household use), fungicides (e.g., contact fungicides or systemic fungicides, including fungicides for household use), nematicides (e.g., contact nematicides or systemic nematicides, including nematicides for household use) and other pesticides (for example, avicides, molluscicides, piscicides) or biocides (for example, agents for killing bacteria, algae or snails); as well as fertilizers; growth regulators such as plant hormones; micro-nutrients, safeners; pheromones; repellants; baits (e.g., insect baits or snail baits); and/or active principles that are used to modulate (i.e., increase, decrease, inhibit, enhance and/or trigger) gene expression (and/or other biological or biochemical processes) in or by the targeted plant (e.g., the plant to be protected or the plant to be controlled). Agrochemically active substances include chemicals, but also nucleic acids (e.g., single-stranded or double-stranded RNA, such as, for example, used in the context of RNAi technology), peptides, polypeptides, proteins (including seed-binding proteins or antigen-binding proteins) and micro-organisms. "Micro-organisms" as used herein means bacteria, fungi, yeasts, viruses and the like. Examples of such agrochemically active substances will be clear to the skilled person and, for example, include, without limitation: glyphosate, paraquat, metolachlor, acetochlor, mesotrione, 2,4-D, atrazine, glufosinate, sulfosate, fenoxaprop, pendimethalin, picloram, trifluralin, bromoxynil, clodinafop, fluoroxypyr, nicosulfuron, bensulfuron, imazetapyr, dicamba, imidacloprid, thiamethoxam, fipronil, chlorpyrifos, deltamethrin, lambda-cyhalotrin, endosulfan, methamidophos, carbofuran, clothianidin, cypermethrin, abamectin, diflufenican, spinosad, indoxacarb, bifenthrin, tefluthrin, azoxystrobin, thiamethoxam, tebuconazole, mancozeb, cyazofamid, fluazinam, pyraclostrobin, epoxiconazole, chlorothalonil, copper fungicides, trifloxystrobin, prothioconazole, difenoconazole, carbendazim, propiconazole, thiophanate, sulphur, boscalid and other known agrochemicals or any suitable combination(s) thereof. Other suitable agrochemicals will be clear to the skilled person based on the disclosure herein, and may, for example, be any commercially available agrochemical, and, for example, include each of the compounds listed in Phillips McDougall, AgriService November 2007 V4.0, Products Section—2006 Market, Product Index pp. 10-20. The agrochemically active substances can occur in different forms including, but not limited to, crystals, micro-crystals, nano-crystals, co-crystals, a dust, granules, a powder, tablets, a gel, a soluble concentrate, an emulsion, an emulsifiable concentrate, a suspension, a suspension concentrate, a suspoemulsion, a dispersion, a dispersion concentrate, a microcapsule suspension or any other form or type of agrochemical formulation clear to those skilled in the art. Agrochemically active substances not only include active substances or principles that are ready to use, but also precursors in an inactive form, which may be activated by outside factors. As a non-limiting example, the precursor can be activated by pH changes, caused by plant wounds upon insect damage, by enzymatic action caused by fungal attack, or by temperature changes or changes in humidity.

The agrochemical composition hereof may be in a liquid, semi-solid or solid form and, for example, be maintained as an aerosol, flowable powder, wettable powder, wettable granule, emulsifiable concentrate, suspension concentrate, microemulsion, capsule suspension, dry microcapsule, tablet or gel or be suspended, dispersed, emulsified or otherwise brought in a suitable liquid medium (such as water or another suitable aqueous, organic or oily medium) for storage or application. The agrochemical composition hereof comprises at least one, preferably more, antigen-binding proteins hereof. The presence of one or more antigen-binding proteins hereof in the agrochemical composition hereof, ensures the binding of the agrochemically active substance to its site of action, such as the plant or plant part (e.g., the fruit, tuber or bulb), the plant seed or other plant-derived organic material, while sticking of the agrochemically active substance to storage containers and/or operator's equipment is avoided. Optionally, the composition further comprises one or more further components such as, but not limited to, diluents, solvents, adjuvants, surfactants, wetting agents, spreading agents, oils, stickers, thickeners, penetrants, buffering agents, acidifiers, anti-settling agents, anti-freeze agents, photo-protectors, defoaming agents, biocides and/or drift control agents or the like, suitable for use in the composition hereof.

An eighth aspect hereof is a kit of parts for the detection and/or determination of the concentration of one or more polysaccharides, comprising at least one antigen-binding protein hereof.

Possibly, the kit of parts also comprises reagents needed for the labeling and/or detection and/or quantification of the antigen-binding protein.

A ninth aspect hereof is a biosensor for the detection and/or determination of the concentration of one or more polysaccharides, comprising at least one antigen-binding protein hereof.

Preferably, the antigen-binding protein is immobilized on the sensing layer of the biosensor; the detection of the binding can be, as a non-limiting example, optical, electrochemical, by quartz crystal microbalance, by magneto immune-sensors or by micromechanical cantilever-based immunosensors.

The technology for the immobilization of the antigen-binding protein and for the detection of the antigen—antigen-binding protein binding is known to the person skilled in the art and has been reviewed, amongst others, by Marquette and Blum (2006), Fritz (2008) and Skottrup et al. (2008).

A tenth aspect hereof is a targeting agent capable of binding a compound to a plant seed, wherein the targeting agent comprises at least one seed-binding protein hereof.

A "targeting agent," as used herein, is a molecular structure, preferably, with a polypeptide backbone, comprising at least one seed-binding protein, preferably, an antigen-binding protein hereof. A targeting agent in its simplest form consists solely of one single seed-binding protein; however, a targeting agent can comprise more than one seed-binding protein and can be monovalent or multivalent and monospecific or multispecific, as further defined. Apart from one single or multiple seed-binding proteins, a targeting agent can further comprise other moieties, which can be either chemically coupled or fused, whether N-terminally or C-terminally or even internally fused, to the antigen-binding protein. The other moieties include, without limitation, one or more amino acids, including labeled amino acids (e.g., fluorescently or radioactively labeled) or detectable amino acids (e.g., detectable by an antibody), one or more monosaccharides, one or more oligosaccharides, one or more polysaccharides, one or more lipids, one or more fatty acids, one or more small molecules or any combination of the foregoing. In one preferred embodiment, the other moieties function as spacers or linkers in the targeting agent.

A "compound" as used herein can be any compound, preferably, an active substance including, but not limited to, proteins and protein complexes such as enzymes, or chemical compounds including, but not limited to, agrochemical active substances, as earlier defined. Preferably, the compound is a plant-enhancing agent, as earlier defined. Alternatively, a compound may be comprised in or onto a carrier, preferably a microcarrier, wherein the carrier can be coupled, as earlier defined, with one or more targeting agents comprising at least one antigen-binding protein hereof. "Comprised in a carrier" as used herein means bound on or contained in by means such as, but not limited to, embedding, encapsulation and adsorption. Preferably, the carrier is such that the one or more compounds can be incorporated, encapsulated or included into the carrier, e.g., as a nanocapsule, microcapsule, nanosphere, micro-sphere, liposome or vesicle. Preferably, the carriers are such that they have immediate or gradual or slow release characteristics, for example over several minutes, several hours, several days or several weeks. Also, the carriers may be made of materials (e.g., polymers) that rupture or slowly degrade (for example, due to prolonged exposure to high or low temperature, sunlight, high or low humidity or other environmental factors or conditions) over time (e.g., over minutes, hours, days or weeks) and so release the compound from the carrier.

The targeting agent hereof may either be a "mono-specific" targeting agent or a "multi-specific" targeting agent. By a "mono-specific" targeting agent is meant a targeting agent that comprises either a single antigen-binding protein, or that comprises two or more different antigen-binding proteins that each are directed against the same binding site. Thus, a mono-specific targeting agent is capable of binding to a single binding site, either through a single antigen-binding protein or through multiple antigen-binding proteins. By a "multi-specific" targeting agent is meant a targeting agent that comprises two or more antigen-binding proteins that are each directed against different binding sites. Thus, a "bi-specific" targeting agent is capable of binding to two different binding sites. A "tri-specific" targeting agent is capable of binding to three different binding sites, and so on for "multi-specific" targeting agents. Also, in respect of the targeting agents described herein, the term "monovalent" is used to indicate that the targeting agent comprises a single antigen-binding protein. The term "bivalent" is used to indicate that the targeting agent comprises a total of two single antigen-binding proteins. The term "trivalent" is used to indicate that the targeting agent comprises a total of three single antigen-binding proteins, and so on for "multivalent" targeting agents.

"Capable of binding a compound to a plant seed," as used herein, means that the binding of the seed-binding protein, preferably, the antigen-binding protein comprised in the targeting agent to the plant seed, is strong enough to bind, more preferably, to retain (as defined above), the compound, preferably, the plant-enhancing agent, to a plant seed. Preferably, the compound is comprised into or onto a carrier, more preferably, a microcarrier. Preferably, the targeting agent is coupled by affinity binding or by covalent binding to the compounds, even more preferably, to the carrier containing the compounds, preferably, the plant-enhancing agents.

Methods to couple the compound, preferably, the plant-enhancing agent, and/or carrier to the targeting agent are known to the person skilled in the art, and include, but are not limited to, covalent binding and affinity binding. An example of covalent binding is a fusion protein, wherein the targeting agent and a compound of proteinaceous nature are produced, preferably, by means of recombinant protein expression, as one unity. An alternative approach to using fusion proteins is to use chemical cross-linking of residues in the targeting agent for covalent attachment to the compound, which can be a second protein or another chemical compound, using conventional coupling chemistry, for example, as described by Fipula (2007) and in *Bioconjugate Techniques*, Hermanson, ed. Academic Press Inc., San Diego, Calif., USA (2008). Amino acid residues incorporating sulphydryl groups, such as cysteine, may be covalently attached using a bispecific reagent such as succinimidyl maleimidophenylbutyrate (SMPB), for example. Alternatively, lysine groups located at the protein surface may be coupled to activated carboxyl groups on the second protein by conventional carbodiimide coupling using 1-ethyl-3-[3-dimethylaminopropyl] carbodiimide (EDC) and N-hydroxysuccinimide (NHS). The coupling between the targeting agent and the compound or carrier wherein the compound is comprised, may be direct, or a spacer or hinge molecule can be used. Examples of such spacers can be found in WO 0024884 and WO 0140310.

One embodiment hereof is the use of a targeting agent, comprising at least one seed-binding protein, preferably, an antigen-binding protein hereof, most preferably, a VHH selected from the group consisting of SEQ. ID NOS:1-11, or any suitable fragment thereof, to retain a plant-enhancing agent to a plant seed. Preferably, the targeting agent is used to retain a plant-enhancing agent to a plant seed during seed treatment, seed storage, seed handling and/or seed planting. Preferably, the targeting agent is coupled, by affinity binding or by covalent binding, to the plant-enhancing agent. Even more preferably, the targeting agent is coupled, by affinity binding or by covalent binding, to a carrier (as described above) wherein the plant-enhancing agent is comprised. This embodiment is especially useful in case a compound needs to be encapsulated, embedded in or absorbed on a matrix for ensuring a slow release of the compound, or to increase the lifetime of the compound, as is the case for the encapsulation of living bacteria such as *Rhizobacteria*.

An eleventh aspect hereof is the use of a targeting agent hereof, to bind a plant-enhancing agent to a plant or a plant part.

"Plant part," as used herein, means any plant part whether part of an intact living or growing plant or whether isolated or separated from an intact living plant, and even dead plant material can be envisaged. Preferably, the plant part is selected from the group consisting of seeds, roots, fruits, cones, bulbs and tubers. More preferably, the plant parts are selected from the group consisting of seeds and fruits. Most preferably, the plant parts are selected from the group of seeds of maize, wheat, sorghum, rye, soybean, rice, cotton, canola, sunflower, sugar beet, potatoes, vegetables, flowers, turf and forage grass and fruits of apple, pear, citrus, banana or stone fruit trees.

In order to be able to bind, preferably, to retain, a plant-enhancing agent to a plant or a plant part, either one single or multiple targeting agents are either fused with or attached to the plant-enhancing agent, either by a covalent bond, by hydrogen bonds, by dipole-dipole interactions, by weak Van der Waals forces or by any combination of the foregoing. "Attached," as used herein, means "coupled to," "connected to," "anchored in," "admixed with" or "covering."

One embodiment hereof is the use of a targeting agent comprising at least one seed-binding protein, preferably, an antigen-binding protein hereof, most preferably, a VHH selected from the group consisting of SEQ. ID NOS:1-11, or any suitable fragment thereof, to retain a plant-enhancing agent to bind a plant-enhancing agent to a plant or a plant part.

Preferably, the plant-enhancing agent is comprised in or onto a carrier, preferably, a microcarrier. Preferably, the seed-binding protein comprised in the targeting agent hereof, is binding to a plant cell wall component comprised in the plant or plant part. Preferably, the plant cell wall component is a polysaccharide, more preferably, the plant cell wall component is a structural polysaccharide or a heteropolysaccharide, most preferably, the plant cell wall component is a pectic polysaccharide.

In one preferred embodiment, the plant cell wall component is comprised in wounded tissue of a plant or a plant part, such as, but not limited to, a wound caused by harvesting methods or by a chewing or sucking insect. In such cases, as a non-limiting example, compounds that kill insects may be targeted to the wound to avoid further damage, or a fungicidal compound or a combination of fungicidal compounds may be targeted to the plant wound to avoid fungal infection of the wounded plant tissue. More preferably, the wounded tissue is comprised in a fruit, a bulb, a tuber or a seed.

A twelfth aspect hereof is the use of a targeting agent hereof to modify plant cell wall components.

"To modify plant cell wall components," as used herein, means to alter the appearance including, but not limited to, the color, the smell, the taste, or the feeling of plant cell wall components (e.g., by binding pigment, fragrance, or softener to the plant cell wall components), to increase or decrease the concentration of one or more plant cell wall components in complex plant cell wall component mixtures (e.g., by targeting degrading enzymes to plant cell wall components or by scavenging certain plant cell wall components), or to create entirely novel plant cell wall components ("designer plant cell wall components"), that are not naturally occurring (e.g., by targeting plant cell wall-modifying enzymes, such as endo-rhamnogalacturonan hydrolase, endo-rhamnogalacturonan lyase, endo-galactanase, endo-arabinase, arbinofuranosidase, galactosidase, or exo-galacturosidase). To "target" as used herein means that the compound is delivered at or near its site of action.

Modifying plant cell wall components may prove useful for improving plants and plant products, for improving processing characteristics and for generating new materials as food ingredients or medical materials. A targeting agent hereof can be useful for modifying plant cell wall components, either when applied directly to mixtures of plant cell wall components or even in vivo in transgenic plants using methods as described in WO 01/59137, incorporated herein for reference.

In one embodiment, the targeting agent hereof is a fusion protein. Fusion proteins are known to the person skilled in the art and consist of two or more proteins, protein parts or peptides that are joined together, either by chemical means (such as by cross-linking or by covalent binding) or by recombinant DNA methods. Fusion proteins are particularly useful as they add certain functional characteristics to the fusion partner, e.g., increase the solubility or modify the substrate specificity. A fusion protein hereof, comprises at least one antigen-binding protein hereof, wherein the antigen-binding protein provides certain characteristics, e.g., its affinity for plant cell wall components, to its fusion partner. In one preferred embodiment, the antigen-binding protein comprised in the fusion protein allows the targeting of the fusion protein to a plant cell wall component, such as the targeting of a lignin-degrading enzyme to lignin in a substrate mix for bioethanol production. In another embodiment, the antigen-binding protein comprised in the fusion protein allows the immobilization of the fusion protein onto any type of solid matrix, which is particularly useful for purification of the fusion protein, e.g., an antigen-binding protein binding to sepharose for purification on sepharose matrices.

A last aspect hereof is an agrochemical composition comprising at least one targeting agent hereof.

Preferably, the agrochemical composition (as defined above) is a composition for seed treatment. Preferably, the targeting agent comprises more than one seed-binding protein. The combination of more than one seed-binding protein into one targeting agent may have as additional benefit either that the seed binding is stronger or that it is more specific.

E1 Lime pectin, DE 11%
F1 Lime pectin, DE 43%
G1 Lime pectin, DE 0%
H1 Lime pectin, DE 16%
I2 RGII enriched pectin (red wine)
I3 Seed mucilage (Arabidopsis)
H4 RGI #5 (potato)

Figure 5:
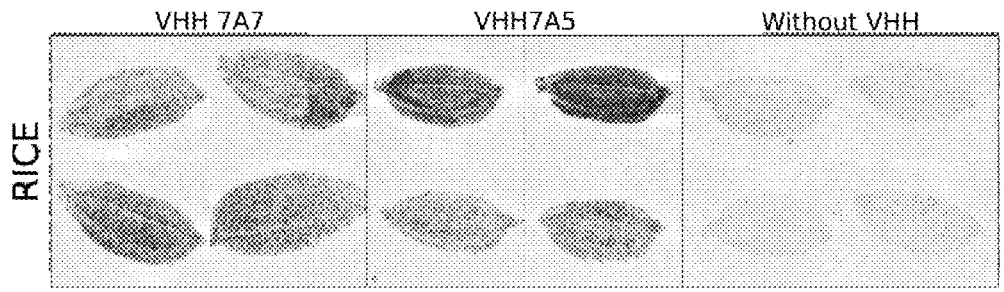
Figure 5:
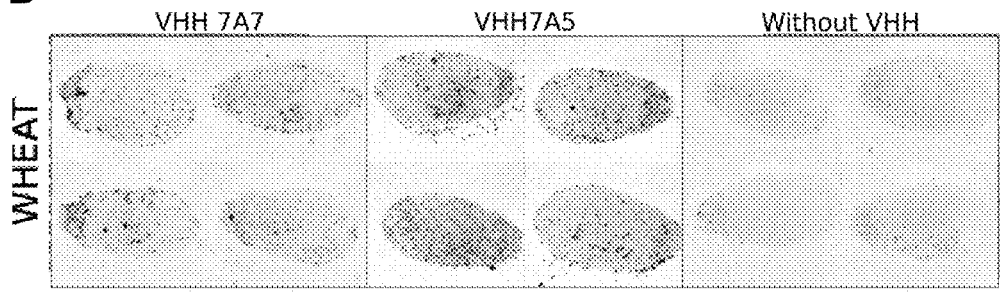
Figure 5:
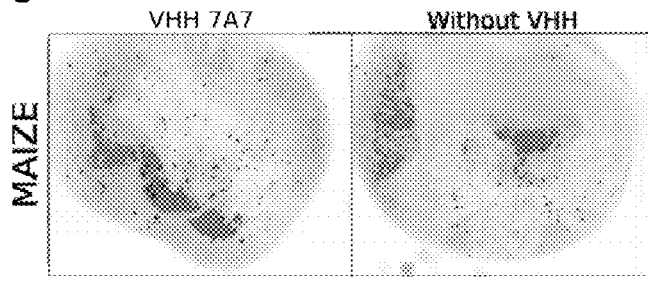

FIG. 5: Binding of microcapsules to crop seeds. Rice (A), wheat (B), and maize (C) seeds were incubated with seed-binding VHH coupled to fluorescent microcapsules. Microcapsules without VHH are shown for each crop seed as control condition.

FIG. 6: Binding of microcapsules to damaged sites of apple skin and damaged potato plant leaf surface. Discs of apple skin and potato leaf were incubated with seed and wounded tissue-binding VHH coupled to fluorescent microcapsules. Microcapsules were bound predominantly to sites of damage on fruit or wounded tissue on plants.

DETAILED DESCRIPTION

Examples

Example 1

Generation and Selection of VHH

Immunization of Llamas with Potato Leaf Homogenate, or Wheat Leaf Homogenate

With the aim of generating an immune response against surface-exposed plant materials, llamas were immunized with potato leaf homogenate or wheat leaf homogenate as follows: homogenized leaves from potato plants (*Solanum tuberosum* variety Desiree) or wheat plants (*Triticum aestivum* variety Boldus) were prepared by freezing leaves in liquid nitrogen and homogenizing the leaves with mortar and pestle until a fine powder was obtained. Bradford protein assay was used to determine the total protein concentration. Aliquots were made, stored at −80° C., and suspensions were used for immunization.

Llamas were immunized at weekly intervals with six intramuscular injections of homogenized potato leaves, or homogenized wheat leaves, according to standard procedures. Three llamas, "407928," "Chilean Autumn" and "Niagara," were immunized with homogenized potato leaves and another two llamas, "33733" and "Organza," were immunized with homogenized wheat leaves. Llamas "407928" and "33733" were immunized using Adjuvant LQ (Gerbu), and llamas "Chilean Autumn," "Niagara" and "Organza" were immunized using Freund's Incomplete Adjuvant (FIA). Doses for immunizations of llamas "407928" and "33733" were 1 mg total protein for each day 0, 7, 14, 21, 28, 36, and PBL were collected at day 40. At time of PBL collection at day 40, sera of llamas "407928" and "33733" were collected. Doses for immunizations of llamas "Chilean Autumn," "Niagara" and "Organza" were 100 μg total protein for day 0, and 50 μg for days 7, 14, 21, 28, and 35. At day 0, day 25, and at time of PBL collection at day 38, sera of llamas "Chilean Autumn," "Niagara" and "Organza" were collected.

Library Construction—

From each immunized llama a separate VHH library was made. RNA was isolated from peripheral blood lymphocytes, followed by cDNA synthesis using random hexamer primers and Superscript III according to the manufacturer's instructions (Invitrogen). A first PCR was performed to amplify VHH and VH using a forward primer mix [1:1 ratio of cal1001 (5'-gtcctggctgctcttctacaagg-3') SEQ ID NO: 12 and cal1001b (5'-cctggctgctcttctacaaggtg-3') SEQ ID NO: 13] and reverse primer cal1002 (5'-ggtacgtgctgttgaactgtcc-3') SEQ ID NO: 14. After isolation of the VHH fragments a second PCR was performed using forward primer A6E (5'-gatgtgcagctgcaggagtctggrggagg-3') SEQ ID NO: 15 and reverse primer 38 (5'-ggactagtgcggccgctggagacggt-gacctgggt-3') SEQ ID NO: 16. The PCR fragments were digested using PstI and Eco91I restriction enzymes (Fermentas), and ligated upstream of the pIII gene in vector pMES4 (GenBank: GQ907248.1). The ligation products were ethanol precipitated according to standard protocols, resuspended in water, and electroporated into TG1 cells. Library sizes ranged from 1E+08 to 6E+08 independent clones. Single colony PCR on randomly picked clones from the libraries was performed to assess insert percentages of the libraries. All libraries had ≥90% insert percentages except for the library from immunized llama "Organza," which had an insert percentage of 80%. Libraries were numbered 27, 28, 29, 31, 32 for llamas "407928," "33733," "Chilean Autumn," "Niagara," and "Organza," respectively. Phage from each of the libraries were produced using VCSM13 helper phage according to standard procedures.

Phage Selections Against Plant Cell Wall Component-Enriched Extracts or Whole Leaves Potato leaf extracts enriched in plant cell wall components were prepared from cuticle and adhering epidermis, removed in thin strips from stems of potato plants. Wheat leaf extracts enriched in plant cell wall components were prepared from cuticle and adhering epidermis, removed in thin strips from wheat sheath leaves. Extracts enriched in pectic polysaccharides were extracted using CDTA (Moller et al., 2007). Strips were frozen in liquid nitrogen and ground with mortar and pestle until fine powders were obtained. Pectic polysaccharides-enriched extracts were prepared by resuspending the fine powders in 50 mM CDTA pH 6.5 using 10 ml per gram of ground material and head-over-head rotation at 4° C. for 30 minutes. Extract and insoluble material were separated using a syringe adapted with a filter. The extracts were further cleared by centrifugation in a micro centrifuge at 20,000 g for 5 minutes.

First round selections against potato epidermal CDTA extract were performed in wells of a 96-well plate (Maxisorp, Nunc) coated with ten-fold or 1000-fold diluted potato epidermal CDTA extract in 0.1 M carbonate buffer pH 8.3 for both the first and second selection rounds. Coatings were performed at 4° C. overnight. Wells were washed three times with PBS/0.05%-TWEEN®-20 and blocked with 5% skimmed milk in PBS (5% MPBS). Phage were suspended in 2.5% MPBS and approximately 2E+11 cfu were used for each well. After binding to the wells at room temperature for 2 hours, unbound phage were removed by extensive washing with PBS/0.05%-TWEEN®-20 and PBS. Bound phage were eluted at room temperature with 0.1 mg/ml trypsin (Sigma) in PBS for 30 minutes. Eluted phage were transferred to a polypropylene 96-well plate (Nunc) containing excess AEBSF trypsin inhibitor (Sigma). The titers of phage from target-coated wells were compared to titers of phage from blank wells to assess enrichments. Phage were amplified using fresh TG1 cells according to standard procedures. Enrichments in selection round 1 were 1E+03, 20, 20, 15, and five-fold for libraries 27, 28, 29, 31, 32, respectively, and >100-fold for all libraries in selection round 2. Selections against wheat epidermal CDTA extract were performed similarly to the selections against potato epidermal CDTA extract but wells were coated with twenty-fold and 2000-fold diluted wheat epidermal CDTA extract for both the first and second selection rounds. Enrichments in selection round 1 were >100, >10, 1, 10, and 5-fold for libraries 27, 28, 29, 31, 32, respectively. Enrichments in selection round 2 were >ten-fold for library 29 and >100-fold for libraries 27, 28, 31, and 32. Selections against potato leaves were performed in two consecutive selection rounds using leaf particles in round 1 and whole leaves in round 2. Libraries 27, 28, 29, 30, 31, and 32 were used for selections against leaves. The leaf particles for first round selections were prepared by blending potato leaves in PBS using an Ultra-Turrax T25 homogenizer. The leaf particles were collected from the suspension by centrifugation. The supernatant, called here "homogenized leaf soluble fraction," is assumingly enriched in intracellular components and was used in solution during phage selection to compete out binders to intracellular epitopes.

Library phage were pre-incubated with the homogenized leaf soluble fraction in 2% MPBS using head-over-head rotation at room temperature for 30 minutes. The mixtures were added to leaf particles and incubated with head-over-head rotation at room temperature for 2 hours. Leaf particles with bound phage were collected by centrifugation and supernatants were discarded. Leaf particles with bound phage were washed extensively by consecutive washes with PBS. Washes were performed by resuspending leaf particles in PBS, spinning down leaf particles, and discarding supernatants. Elution of phage and infection of TG1 were performed as before. For the second selection round whole intact leaves were used. Leaves were incubated floating upside-down on phage solutions in 2% MPBS and phage were allowed to bind at room temperature for 2 hours. The leaves were washed extensively by transferring leaves to fresh tubes with PBS. Elution of bound phage was performed with 100 mM TEA in water, and solutions with eluted phage were neutralized using half of the eluted phage volume of 1 M Tris pH 7.5. Infection of TG1 was performed as before.

Picking Single Colonies from Selection Outputs—

Individual clones were picked from first and second round selections against potato epidermal CDTA extract: a total of 321 clones were picked after both first and second round selections from all libraries. From selections against wheat epidermal CDTA extract a total of 162 clones were picked after second round selections from all libraries. From potato leaf selections a total of 184 clones were picked after second round selections from libraries 27, 28, 29, 31, and 32. Fresh TG1 cells were infected with serially diluted eluted phage and plated on LB agar; 2% glucose; 100 µg/ml ampicillin. Single colonies were picked in 96-well plates containing 100 µl per well 2×TY; 10% glycerol; 2% glucose; 100 µg/ml ampicillin. Plates were incubated at 37° C. and stored at −80° C. as master plates.

Example 2

Characterization of the VHH

Single-Point Binding ELISA—

A single-point binding ELISA was used to identify clones that bind to plant extracts. VHH-containing extracts for ELISA were prepared as follows. 96-well plates with 100 µl per well 2×TY, 2% glucose 100 µg/ml ampicillin were inoculated from the master plates and grown at 37° C. overnight. Twenty-five µl per well of overnight culture was used to inoculate fresh 96-well deep-well plates containing 1 ml per well 2×TY; 0.1% glucose; 100 µg/ml ampicillin. After growing at 37° C. in a shaking incubator for 3 hours, IPTG was added to 1 mM final concentration and recombinant VHH was produced during an additional incubation for 4 hours. Cells were spun down by centrifugation at 3,000 g for 20 minutes and stored at −20° C. overnight. Cell pellets were thawed, briefly vortexed, and 125 µl per well of room temperature PBS was added. Cells were resuspended on an ELISA shaker platform at room temperature for 15 minutes. Plates were centrifuged at 3,000 g for 20 minutes and 100 µl per well of VHH-containing extract was transferred to polypropylene 96-well plates (Nunc) and stored at −20° C. until further use.

Binding of clones from potato epidermal CDTA extract selections was analyzed on both potato epidermal CDTA extract and wheat epidermal CDTA extract using ELISA plates coated with 100 µl per well of thirty-fold diluted potato and thirty-fold wheat epidermal CDTA extracts in 0.1 M carbonate pH 8.3. Binding of clones from wheat epidermal CDTA extract selections was analyzed using ELISA plates coated with 100 µl per well of twenty-fold diluted wheat epidermal CDTA extract in 0.1 M carbonate pH 8.3. After coating at 4° C. overnight and continued coating at room temperature for 1 hour on the next day, plates were washed three times with PBS/0.05%-TWEEN®-20 and blocked with 5% skimmed milk in PBS for 1.5 hours. Plates were emptied and filled with 90 µl per well 1% MPBS. Ten µl of VHH-containing extract from each clone was added to (an) antigen-coated well(s) and a blank well. VHH were allowed to bind at room temperature for 1 hour and unbound VHH were removed by washing three times with PBS/0.05%-TWEEN®-20. Bound VHH were detected with sequential incubations with monoclonal mouse anti-histidine antibodies (Abd Serotec) in 1% MPBS/0.05%-TWEEN®-20 and rabbit anti-mouse IgG whole molecule antibodies conjugated with alkaline phosphatase (RaM/AP) (Sigma) in 1% MPBS/0.05%-TWEEN®-20 Unbound antibodies were removed by washing three times with PBS/0.05%-TWEEN®-20 after each antibody incubation. The plates were washed an additional two times with PBS and 100 µl pNPP disodium hexahydrate substrate (Sigma) was added to each well.

The absorbance at 405 nm was measured and the ratio of VHH bound to (a) target-coated well(s) and a non-target-coated well was calculated for each clone. 23% of clones had a ratio greater than 2 and these clones were firstly picked for more detailed characterization. A second group of clones with a ratio between 1.15 and 2, and comprising 10% of all clones, was revisited later. Clones with a ratio less than 1.15 were not analyzed further.

For clones from whole leaf selections an adapted ELISA was developed. Upside-down floating leaf discs were used instead of coating wells with antigen. Incubations were similar to the extracts ELISA. After incubation with the substrate the leaf discs were removed from the wells using a forceps and the absorbance at 405 nm was measured. Signals obtained for each clone were compared to signals obtained from wells with leaf discs without primary antibody incubation and the ratios were calculated. A leaf surface-binding antibody that was found and characterized from epidermal extract selections was used as positive control antibody. VHH with a ratio greater than 1.5 were analyzed further by sequencing.

Single Colony PCR and Sequencing—

Single colony PCR and sequencing was performed on ELISA positive clones as follows. Cultures from master plate wells with ELISA positive clones were diluted ten-fold in sterile water. Five W from these diluted clones were used as template for PCR using forward primer MP57 (5'-ttatgcttccggctcgtatg-3') SEQ ID NO: 17 and reverse primer GIII (5'-ccacagacagccctcatag-3') SEQ ID NO: 18. PCR products were sequenced by Sanger-sequencing using primer MP57 (VIB Genetic Service Facility, University of Antwerp, Belgium). From selections against plant cell wall component-enriched extracts VHH 6D7, VHH 7A5, VHH 6B5, VHH 6D11, VHH 6F2, VHH 6H4, VHH 7A7, VHH 7E9, VHH 8A4, and VHH 8D6 were found. Clones VHH 6B5, VHH 6D11, VHH 6F2, VHH 6H4 are single amino acid variants of VHH 7A5. VHH 7E9 is a single amino acid variant of VHH 7A7. VHH 8A4 and VHH 8D6 are single amino acid variants of each other. From selections against leaf particles and whole leaves VHH 12C3 was found.

Antibody Production and Purification—

VHH were produced in *E. coli* suppressor strain TG1 or non-suppressor strain WK6 (Fritz et al., *Nucleic Acids Research*, Volume 16 Number 14 1988) according to standard procedures. Briefly, colony streaks were made and overnight cultures from single colonies inoculated in 2×TY; 2% glucose; 100 µg/ml ampicillin. The overnight cultures were used to inoculate fresh cultures 1:100 in 2×TY; 0.1% glucose; 100 µg/ml ampicillin. After growing at 37° C. in a shaking incubator for 3 hours, IPTG was added to a 1 mM final concentration and recombinant VHH were produced during an additional incubation for 4 hours. Cells were spun down and resuspended in $\frac{1}{50}^{th}$ of the original culture volume of periplasmic extraction buffer (50 mM phosphate pH 7; 1 M NaCl; 1 mM EDTA) and incubated with head-over-head rotation at 4° C. overnight. Spheroplasts were spun down by centrifugation at 3,000 g and 4° C. for 20 minutes. Supernatants were transferred to fresh tubes and centrifuged again at 3,000 g and 4° C. for 20 minutes. Hexahistidine-tagged VHH were purified from the periplasmic extract using $\frac{1}{15}^{th}$ of the extract volume of TALON metal affinity resin (Clontech), according to the manufacturer's instructions. Purified VHH were concentrated and dialyzed to PBS using Vivaspin 5 kDa molecular weight cut-off (MWCO) devices (Sartorius Stedim), according to the manufacturer's instructions.

Example 3

VHH Binding to Plant Seeds

Binding of VHH to Untreated Crop Seeds—

Binding of VHH antibody fragments to a wide variety of crop seeds was investigated using maize, tomato, rice, and wheat seeds. Tomato, rice, and wheat seeds were incubated in quadruplicate with solutions containing 2.5-5 lag/ml hexahistidine-tagged VHH in 1% BSA in PBS and incubated in a 96-well 0.45 µm deep-well filtration plate (Millipore) for 1 hour with gently rocking on an ELISA shaking platform. Control conditions included incubations with unrelated non-seed-binding VHH and incubations without VHH. Solutions containing non-bound VHH were removed using a filtration plate setup (Millipore). Bound VHH were detected with sequential incubations with monoclonal mouse anti-histidine antibodies (Abd Serotec) in 1% BSA in PBS and rabbit anti-mouse IgG whole molecule antibodies conjugated with alkaline phosphatase (RaM/AP) (Sigma) in 1% BSA in PBS. Five sequential washes were performed between each antibody incubation. Washes were performed by incubation with PBS and gentle rocking on an ELISA shaking platform. Wash solutions were removed using the filtration plate setup. pNPP disodium hexahydrate substrate (Sigma) was added to each well and allowed to react until coloring of the substrate was clearly visible (5-25 minutes). Substrates were collected using the filtration plate setup and the absorbance at 405 nm was measured and signal of seed-binding VHH compared to coloring of the substrate with blank seeds and seeds treated with unrelated control VHH. Clear and reproducible VHH binding to crop seeds such as rice, wheat, and tomato was observed, i.e., for VHH 7A7 and 12C3 (see Table 1).

Figure 1:
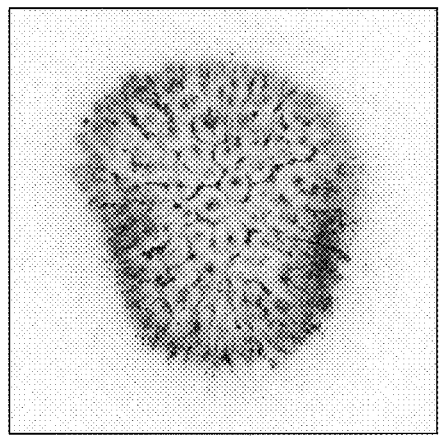
FIG. 1: VHH binding to native *Arabidopsis* seeds imaged by confocal microscopy with spectral imaging and linear unmixing. Seed auto fluorescence and Alexa488 spectra were recorded and assigned different pseudo colors. Seeds were incubated with VHH 6D7 and bound VHH were detected with anti-histidine/Alexa488-conjugated antibodies. Specific binding signal of VHH to seed is shown only.

A similar assay was performed to investigate binding of VHH antibody fragments to maize seeds. Maize seeds were incubated in quadruplicate with solutions containing 2.5-5 µg/ml hexahistidine-tagged VHH in 1% BSA in PBS and incubated in 2-ml reaction tubes or wells of a 12-well plate for 1 hour with gently rocking on an ELISA shaking platform. Control conditions included incubations with unrelated non-seed-binding VHH and incubations without VHH. Solutions containing non-bound VHH were removed using a vacuum aspiration system. Bound VHH were detected with sequential incubations with monoclonal mouse anti-histidine antibodies (Abd Serotec) in 1% BSA in PBS and rabbit anti-mouse IgG whole molecule antibodies conjugated with alkaline phosphatase (RaM/AP) (Sigma) in 1% BSA in PBS. Five sequential washes were performed between each antibody incubation. Washes were performed by incubation with PBS and gentle rocking on an ELISA shaking platform. Wash solutions were removed using vacuum aspiration. pNPP disodium hexahydrate substrate (Sigma) was added to each tube or well and allowed to react until coloring of the substrate was clearly visible (5-25 minutes). Substrates were collected and the absorbance at 405 nm was measured and signal of seed-binding VHH compared to coloring of the substrate with blank seeds and seeds treated with unrelated control VHH. Clear and reproducible VHH binding to crop seeds such as maize was observed, i.e., for VHH 7A7 (see Table 1). It was surprising that, although no selections or screenings had been performed against plant seeds, VHH were found that showed clear and specific binding to particular plant seeds.

monoclonal mouse anti-histidine antibodies directly conjugated with Alexa-488 fluorescent dye (Abd Serotec) in 5% MPBS for 1 hour. Unbound antibodies were removed by washing five times with PBS. Seeds were placed in 18-well µ-slides and analyzed by microscopy. Clear binding of various VHH to the surface of the seeds was observed as exemplified for VHH 6D7 (FIG. 1).

Example 4

Binding of VHH to Wounded Plant Tissue

Figure 2:
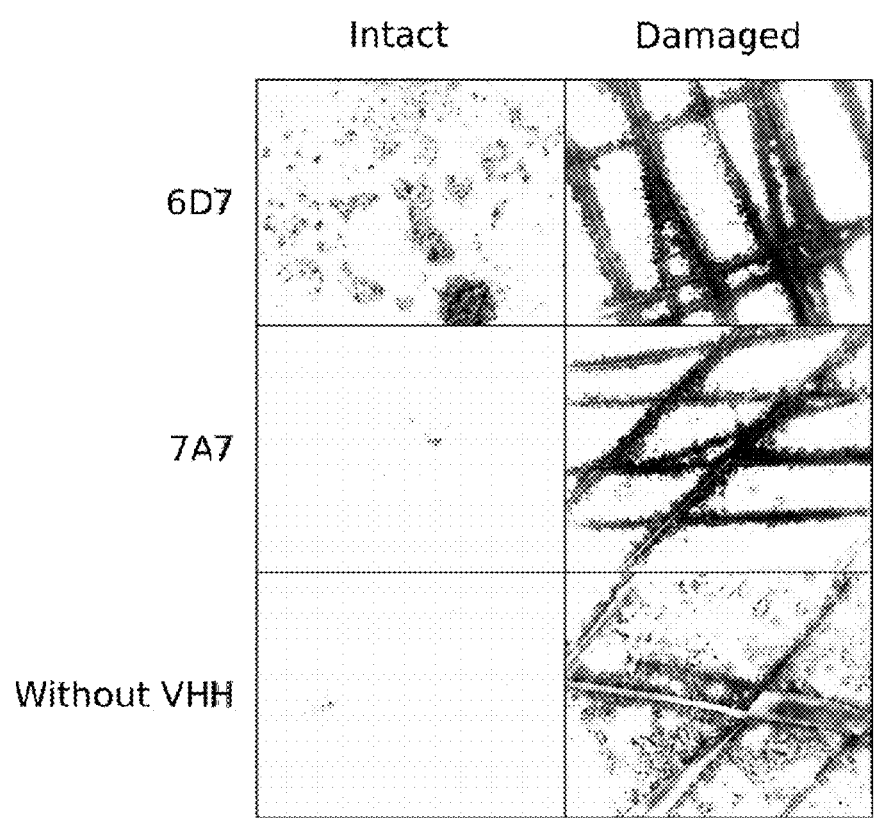
FIG. 2: VHH binding to damaged sites of apple skin. Discs of apple skin were made using a puncher tool and incubated with various VHH. Bound VHH were detected by incubation with monoclonal mouse anti-histidine antibodies directly conjugated with Alexa-488 fluorescent dye.

Binding of VHH to Damaged Apple Skin—
VHH binding to damaged apple skin discs was investigated. Discs of untreated apple skin were prepared by punching apple skin with a puncher tool. A series of apple skin discs was purposely damaged by making cuts into the outer surface of apple skin discs. Binding of each antibody to damaged apple skin was investigated in separate incubations for each antibody in comparison with intact apple skin as a control. Apple skin discs were put upside-down in wells of a multi-well plate containing PBS. PBS was removed from the wells and fresh PBS was added to each well. This wash cycle was repeated two times. Solutions containing 5 µg/ml VHH in 1% BSA in PBS were added to the skin discs and incubated for 60-90 minutes. Unbound VHH were removed by washing five times with PBS. Bound VHH were detected by incubation with monoclonal mouse anti-histidine antibodies directly conjugated with Alexa-488 fluorescent dye (Abd Serotec) in 1% BSA in PBS for 1 hour. Unbound antibodies were removed by washing five times with PBS. Apple skin discs were placed in Petri dishes and analyzed by microscopy on a macrozoom microscope system (Nikon). Some VHH, such as VHH 6D7 and VHH 7A7, were found binding predominantly to damaged areas of apple skin discs (FIG. 2).

TABLE 1

Binding of VHH to crop seeds in quadruplicate. Average values for binding and standard deviation are shown. Control conditions are unrelated VHH and incubations without VHH. Crop seed-binding VHH with different specificity were found.

|  | Wheat Average | Wheat Stdev | Tomato Average | Tomato Stdev | Rice Average | Rice Stdev | Maize Average | Maize Stdev |
| --- | --- | --- | --- | --- | --- | --- | --- | --- |
| 7A7 | 1.021 | 0.083 | 0.423 | 0.068 | 0.991 | 0.098 | 3.428 | 0.426 |
| 12C3 | 0.357 | 0.021 | 0.373 | 0.055 | 0.241 | 0.040 | 0.360 | 0.103 |
| Unrelated VHH | 0.275 | 0.009 | 0.185 | 0.006 | 0.225 | 0.023 | 0.320 | 0.063 |
| no VHH | 0.246 | 0.036 | 0.174 | 0.010 | 0.204 | 0.031 | 0.301 | 0.102 |

Figure 3:
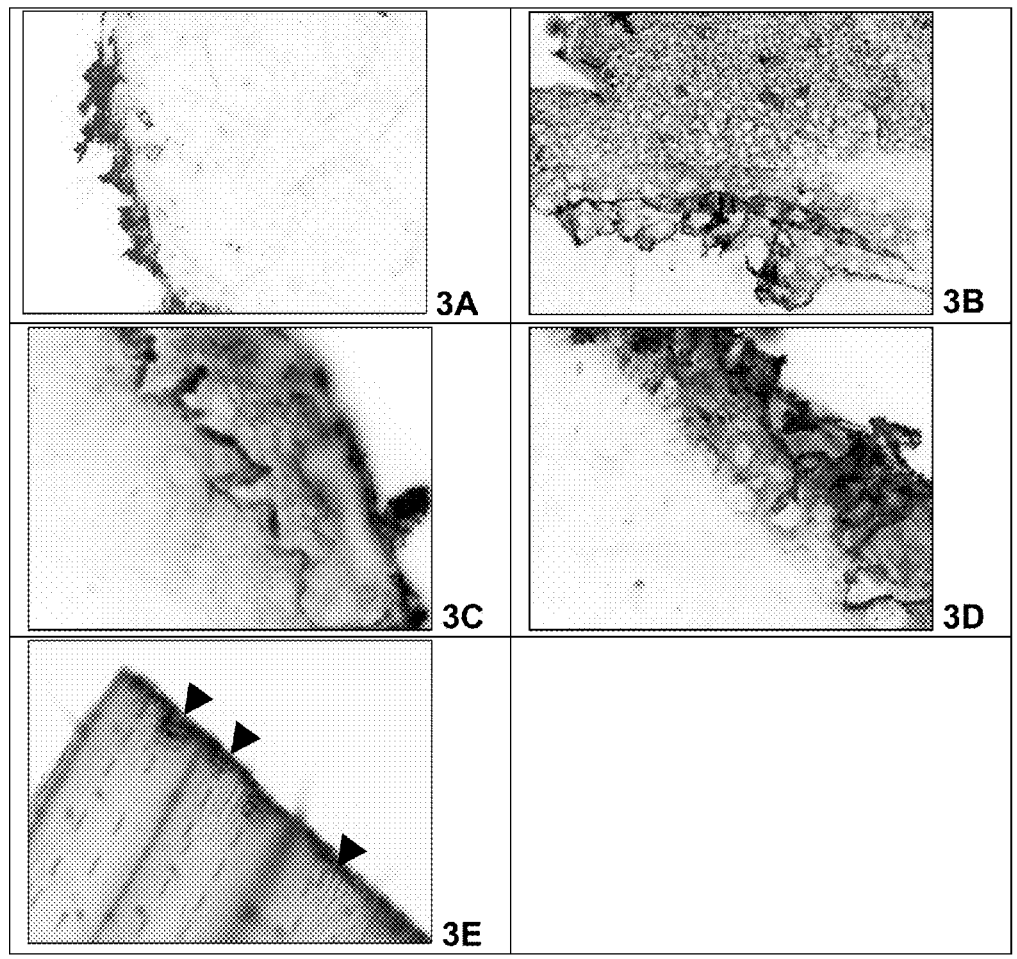
FIG. 3: VHH 6D7 (A), 7A5 (B), 7A7 (C), 7E9 (D) binding to potato leaf punches and VHH 6D7 (E) binding to wheat leaf strip. Leaf punches were made using a puncher tool and incubated with VHH. Strips were cut from a wheat leaf and incubated with VHH. Bound VHH were detected by incubation with anti-histidine/Alexa488-conjugated antibodies. VHH were found to be strongly binding to leaf punches or leaf pieces, predominantly at sites of wounded tissue.

Binding of VHH to *Arabidopsis* Seeds—
Binding of VHH to seeds was analyzed on fixed and non-fixed *Arabidopsis thaliana* seeds and analyzed by microscopy. Seeds were fixed by incubating in 4% paraformaldehyde in 50 mM 1,4-piperazinediethanesulfonic acid (PIPES), 5 mM MgSO4, 5 mM ethylene glycol tetraacetic acid (EGTA) at room temperature for 30 minutes. After fixation seeds were washed three times in PBS. Three washes with PBS were performed for native seeds prior to labeling with antibody fragments. PBS was removed from the wells and solutions of 5 µg/ml VHH in 5% MPBS added and incubated for 60-90 minutes. Unbound VHH were removed by washing five times with PBS. Bound VHH were detected with incubation with Binding of VHH to Wounded Plant Leaves—
VHH binding to non-fixed potato leaf discs, and wheat leaf strips was investigated. Leaf discs were prepared by punching a fresh potato leaf with a puncher tool. Wheat leaf pieces were prepared by cutting approximately 0.25 cm$^2$ leaf pieces. Leaf discs and leaf pieces were put in wells of a 96-well plate containing PBS. PBS was removed from the wells and fresh PBS was added to each well. This wash cycle was repeated two times. Potato leaf discs and wheat leaf pieces were transferred to solutions containing 5 µg/ml VHH in 5% MPBS and incubated for 60-90 minutes. Unbound VHH were removed by washing five times with PBS. Bound VHH were detected with incubation with monoclonal mouse anti-histidine antibodies directly conjugated with Alexa-488 fluorescent dye (Abd Serotec) in 5% MPBS for 1 hour. Unbound antibodies were removed by washing five times with PBS. Leaf discs were placed in 8-well μ-slides and analyzed by microscopy. VHH 6D7, 7A5, 7A7 and 7E9 were found strongly binding to leaf discs or leaf pieces, predominantly at sites of wounded tissue (FIG. 3), which were caused by punching, or cutting leaves.

Example 5

VHH Binding to Polysaccharide-Enriched Plant Extracts in ELISA

VHH Binding to Different Plant Species Extracts and Soybean Soluble Polysaccharides in ELISA—

VHH binding to plant leaf extracts from potato plants (*Solanum tuberosum* variety Désirée), wheat plants (*Triticum aestivum* variety Boldus), ryegrass plants (*Lolium perenne*), pea plants (*Pisum sativum*), black nightshade plants (*Solanum nigrum*), and to soybean soluble polysaccharides was analyzed in ELISA. Whole leaf extracts enriched in cell-wall polysaccharides were extracted using CDTA (Moller et al., 2007). Leaves were frozen in liquid nitrogen and homogenized with mortar and pestle until fine powders were obtained. Cell-wall polysaccharides-enriched extracts were prepared by resuspending the fine powders in 50 mM CDTA pH 6.5 using 10 ml per gram of ground material and head-over-head rotation at 4° C. for 30 minutes. Extract and insoluble material were separated using a syringe adapted with a filter. The extracts were further cleared by centrifugation in a micro centrifuge at 20,000 g for 5 minutes. Crude soybean soluble polysaccharides were extracted according to the method described by Nakamura et al. (2002) and then dissolved in 50 mM CDTA buffer pH 6.5. ELISA plates were coated with thirty-fold diluted CDTA extracts in PBS at 4° C. overnight. Coating was continued at room temperature for 1 hour on the next day. Plates were washed three times with PBS/0.05%-TWEEN®-20 and blocked with 5% skimmed milk in PBS for 1-2 hours. Five lag/ml dilutions of purified VHH were prepared in 1% MPBS/0.05%-TWEEN®-20. Antibody dilutions were transferred to the plant extracts-coated plates and VHH were allowed to bind for 1 hour at room temperature. Bound VHH were detected with sequential incubations with monoclonal mouse anti-histidine antibodies (Abd Serotec) and rabbit anti-mouse IgG whole molecule antibodies conjugated with alkaline phosphatase (RaM/AP) (Sigma) in 1% MPBS/0.05%-TWEEN®-20 Unbound antibodies were removed by washing three times with PBS/0.05%-TWEEN®-20 after each antibody incubation. The plates were washed an additional two times with PBS and 100 μl pNPP disodium hexahydrate substrate (Sigma) was added to each well. The absorbance at 405 nm was measured (see Table 2). The VHH clearly show binding with different specificity to potato, wheat, black nightshade, pea, grass, and soybean soluble polysaccharide extracts. For soybean it has been described that the CDTA-soluble pectic fraction is composed of rhamnogalacturonan and xylogalaturonan, but not homogalacturonan (Huisman et al., 2001). Since uncharacterized crude extracts were used in this ELISA setup, binding to different samples was assessed qualitatively and no direct comparisons between different extracts were made.

TABLE 2

VHH binding to polysaccharide-enriched plant extracts. Data from different experiments were combined for this overview. Control conditions are shown for each. Control conditions include investigating binding of each VHH to a blocked well without coated antigen as well as investigating any possible aspecific binding of the anti histidine and anti-mouse IgG antibodies for each coating condition. Few clones appear in different experiments (6D7, and 7A5).

| VHH ID | Potato CDTA | Wheat CDTA | BLNS CDTA | Pea CDTA | Grass CDTA | SoyBean CDTA | No coat |
|---|---|---|---|---|---|---|---|
| 6D7 | 0.354 | 0.125 | | | | | 0.075 |
| Blank | 0.076 | 0.075 | | | | | 0.075 |
| 7A7 | 1.487 | 0.213 | | | | | 0.105 |
| 7A5 | 0.670 | 0.141 | | | | | 0.075 |
| Blank | 0.087 | 0.076 | | | | | 0.073 |
| 6D7 | 0.187 | 0.164 | 0.182 | 0.235 | | | 0.079 |
| 8A4 | 2.606 | OVER | OVER | OVER | | | 0.079 |
| Blank | 0.078 | 0.079 | 0.078 | 0.072 | | | 0.080 |
| 7A5 | 2.563 | 0.260 | 0.644 | 0.901 | 1.694 | 0.170 | 0.115 |
| 6D7 | 0.954 | 0.256 | 0.391 | 0.321 | 1.066 | 0.212 | 0.158 |
| Blank | 0.234 | 0.131 | 0.141 | 0.116 | 0.128 | 0.166 | 0.110 |
| 8A4 | | | OVER | OVER | OVER | 0.182 | 0.111 |
| Blank | | 0.304 | 0.147 | 0.347 | 0.188 | | 0.118 |

BLNS: black nightshade.
CDTA: Pectic polysaccharide enriched extract.
OVER means ≥4,000.

Example 6

VHH Binding to Plant Cell Wall Components in ELISA

VHH Binding to Pectic Polysaccharides in ELISA—

Binding of arrays of purified VHH to different pectin species was analyzed in ELISA. ELISA plates (Maxisorp, Nunc) were coated with 100 μl per well 100 μg/ml 70-75% esterified apple pectin (Sigma), ≥80% esterified pectin from citrus fruits, 20-34% esterified pectin from citrus fruits (Sigma), or gum arabic (Sigma) as negative control in PBS. Plates were coated at 4° C. overnight and coating was continued at room temperature for 1 hour on the next day. Plates were washed three times with PBS/0.05%-TWEEN®-20 and blocked with 5% skimmed milk in PBS for 1 hour. Purified VHH were diluted to 3 μg/ml in 1% MPBS/0.05%-TWEEN®-20 and added to the pectin-coated plates and VHH were allowed to bind for 1 hour at room temperature. Bound VHH were detected with sequential incubations with monoclonal mouse anti-histidine antibodies (Abd Serotec) and rabbit anti-mouse IgG whole molecule antibodies conjugated with alkaline phosphatase (RaM/AP) (Sigma) in 1% MPBS/0.05%-TWEEN®-20 Unbound antibodies were removed by washing three times with PBS/0.05%-TWEEN®-20 after each antibody incubation. The plates were washed an additional two times with PBS and 100 μl pNPP disodium hexahydrate substrate (Sigma) was added to each well. The absorbance at 405 nm was measured and binding obtained binding profile for all clones compared (see Table 3A). Diverse and distinct binding patterns were observed for different VHH.

VHH Binding to Pectic Polysaccharides in ELISA in Titration—

Figure 4:
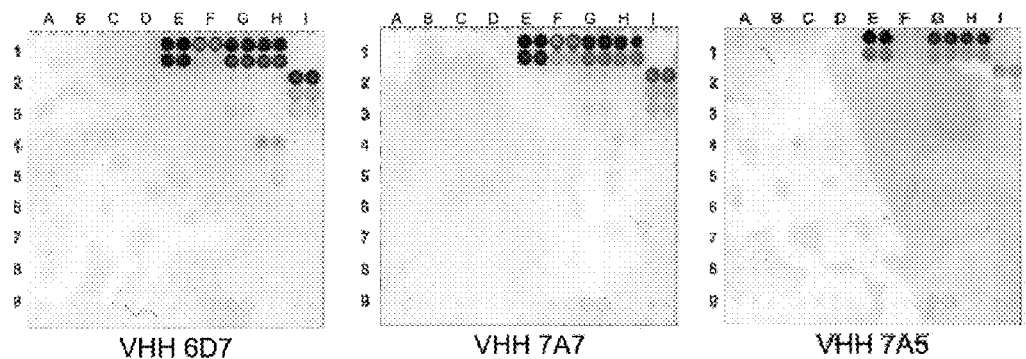
FIG. 4: Binding profiles of VHH on arrays containing 36 bovine serum albumin (BSA)-conjugated oligosaccharides (columns A-D on each array) and 45 polysaccharides (columns E-I on each array) spotted on nitrocellulose. Each sample is represented by four spots on the array (two concentrations in duplicate). Arrays were probed with 5 μg/ml of the selected VHH and bound VHH were detected with secondary anti-histidine and tertiary enzyme-conjugated antibodies. Strong binding signals were observed, predominantly on pectins with low degrees of esterification indicating binding to homogalacturonan epitopes.

Titration of VHH was performed on ELISA plates (Maxisorp, Nunc) coated with 100 μl per well 100 μg/ml 70-75% esterified apple pectin (Sigma) or 20-34% esterified pectin from citrus fruits (Sigma) in PBS. Plates were coated at 4° C. overnight and coating was continued at room temperature for 1 hour on the next day. Plates were washed three times with PBS/0.05%-TWEEN®-20 and blocked with 5% skimmed milk in PBS for 1 hour. Four-fold serial dilutions of purified VHH were prepared in 1% MPBS/0.05%-TWEEN®-20 in polypropylene 96-well plates. Antibody concentrations ranged from 3 µg/ml to 12 ng/ml. Antibody dilutions were transferred to the pectin-coated plates and VHH were allowed to bind for 1 hour at room temperature. Bound VHH were detected with sequential incubations with monoclonal mouse anti-histidine antibodies (Abd Serotec) and rabbit anti-mouse IgG whole molecule antibodies conjugated with alkaline phosphatase (RaM/AP) (Sigma) in 1% MPBS/0.05%-TWEEN®-20. Unbound antibodies were removed by washing three times with PBS/0.05%-TWEEN®-20 after each antibody incubation. The plates were washed an additional two times with PBS and 100 µl pNPP disodium hexahydrate substrate (Sigma) was added to each well. The absorbance at 405 nm was measured and plotted as function of antibody concentration (see Tables 3B and 3C). VHH 7A5, VHH 7A7 and VHH 6D7 were binding low esterified pectin in ELISA in a dose-dependent manner Binding signals on high esterified pectin were lower than for low esterified pectin for VHH 7A5 and VHH 7A7. VHH 6D7 did not show significant binding to high esterified pectin in ELISA. The preferential binding of VHH 7A5, VHH 7A7 and VHH 6D7 to low esterified pectin is in agreement with array data (FIG. 4).

TABLE 3A

VHH binding to low and high esterified pectins and gum arabic in ELISA. Data from different experiments were combined for this overview. Control conditions are shown for each. Control conditions include investigating binding of each VHH to a blocked well without coated antigen as well as investigating any possible aspecific binding of the anti histidine and anti-mouse IgG antibodies for each coating condition.

| VHH ID | Apple pectin, 70-75% esterification | Pectin from citrus fruits, ≥80% esterified | Pectin from citrus fruits, 20-34% esterified | Gum arabic | No coat |
|---|---|---|---|---|---|
| 6D7 | 0.092 | 0.078 | OVER | 0.068 | 0.075 |
| Blank | 0.076 | 0.077 | 0.080 | 0.073 | 0.075 |
| 7A7 | 0.501 | 0.104 | OVER | 0.084 | 0.105 |
| 7A5 | 0.253 | 0.107 | 0.578 | 0.078 | 0.075 |
| Blank | 0.077 | 0.084 | 0.075 | 0.070 | 0.073 |
| 8A4 | 0.087 | 0.133 | 0.093 | 0.081 | 0.084 |
| Blank | 0.095 | 0.115 | 0.091 | 0.082 | 0.087 |
| 12C3 | 0.104 | 0.083 | 0.145 | 0.083 | 0.083 |
| Blank | 0.086 | 0.082 | 0.084 | 0.083 | 0.083 |

OVER means ≥4,000.

TABLE 3B

VHH binding to low esterified citrus fruit pectin in ELISA:

| [VHH] (µg/ml) | 3.0 | 0.75 | 0.19 | 0.047 | 0.012 | 0 |
|---|---|---|---|---|---|---|
| [VHH] (nM) | 200 | 50 | 13 | 3.1 | 0.78 | 0 |
| 20-34% esterified citrus fruit pectin | + | + | + | + | + | + |

| | | 1 | 2 | 3 | 4 | 5 | 6 |
|---|---|---|---|---|---|---|---|
| VHH7A5 | A | 1.996 | 0.225 | 0.189 | 0.142 | 0.137 | 0.096 |
| VHH7A7 | B | 4.000 | 0.980 | 0.477 | 0.219 | 0.146 | |
| VHH6D7 | C | 4.000 | 0.522 | 0.226 | 0.146 | 0.127 | |

TABLE 3C

VHH binding to high esterified apple pectin in ELISA:

| [VHH] (µg/ml) | 3.0 | 0.75 | 0.19 | 0.047 | 0.012 | 0 |
|---|---|---|---|---|---|---|
| [VHH] (nM) | 200 | 50 | 13 | 3.1 | 0.78 | 0 |
| 70-75% esterified apple pectin | + | + | + | + | + | + |

| | | 1 | 2 | 3 | 4 | 5 | |
|---|---|---|---|---|---|---|---|
| VHH7A5 | A | 0.266 | 0.170 | 0.089 | 0.090 | 0.080 | 0.096 |
| VHH7A7 | B | 0.442 | 0.161 | 0.102 | 0.100 | 0.082 | |
| VHH6D7 | C | 0.090 | 0.086 | 0.083 | 0.097 | 0.081 | |

Example 7

Binding of VHH on Oligo- and Polysaccharide Arrays

Probing Oligo- and Polysaccharide Arrays with VHH—
A plant-specific oligo- and polysaccharide array was used for further elucidation of the epitope classes bound by the selected VHH. Thirty-six bovine serum albumin (BSA)-conjugated oligosaccharides and 45 polysaccharides were spotted on nitrocellulose. On the array each sample is represented by four spots (two concentrations in duplicate). Oligo- and polysaccharide arrays were probed with 5 µg/ml of the selected VHH and bound VHH were detected with secondary anti-histidine, and tertiary alkaline phosphate-conjugated antibodies. Pictures of individual arrays were taken and heatmaps recorded for the different VHH incubations (FIG. 4). The binding data showed that the VHH were highly specific pectin binders since they all bound to lime pectin samples with different degrees of esterification (0%, 11%, 16%, 43% for spots G1, E1, H1, F1, respectively). Binding to a less pure rhamnogalacturonan II sample (spot 12) was probably caused by pectin domains present in this sample. The selected VHH bind preferentially to pectin with lower degrees of methyl esterification suggesting binding to homogalacturonan (HG) epitopes. Interestingly, VHH-binding patterns were different from known conventional antibody-binding patterns tested on the same array (i.e., JIM5 (Knox et al., 1990; Willats et al., 2000; Clausen et al., 2003), JIM7 (Knox et al., 1990; Willats et al., 2000; Clausen et al., 2003), JIM8 (Pennell et al., 1991), JIM13 (Knox et al., 1991; Yates, 1996), LM10 (McCartney et al., 2005), LM15 (Marcus et al., 2008), LM18 (Verhertbruggen et al., 2009), LM19 (Verhertbruggen et al., 2009), LM20 (Verhertbruggen et al., 2009)).

Example 8

Binding of VHH Coupled to Microcapsules to Plant Seeds

With the objective to generate VHH-functionalized polyurea microcapsules, VHH were coupled to microcapsules with a core of 1.5% Uvitex OB (Ciba) in benzyl benzoate and a shell with incorporated lysine to surface-expose carboxyl groups. A core of 1.5% Uvitex OB in benzyl benzoate was used for fluorescent visualization of microcapsules. After production of microcapsules, microcapsules were washed with water and stored as capsule suspensions in water. Before coupling of VHH, microcapsules were washed with MES/NaCl buffer (0.1 M MES/0.5 NaCl pH 6) using a 96-well deep-well filtration plate (Millipore) and vacuum manifold (Millipore). A panel of VHH was dialyzed to MES/NaCl buffer and added to a final concentration of 10-70 µM and incubated with the microcapsules for 15-30 minutes. 1-Ethyl-3-[3-dimethylaminopropyl]carbodiimide Hydrochloride (EDC) (Pierce) was dissolved in MES/NaCl buffer and promptly added to a final concentration of 50 mM. VHH were coupled by incubation with continuous mixing at room temperature for 2 hours. The coupling reactions were stopped by adding glycine or Tris-buffer pH 7.5 to a final concentration of 100 mM and incubation at room temperature for 30 minutes. Non-bound VHH were collected using the filtration plate setup using a deep-well collector plate. Microcapsules were washed three times with PBS and resuspended in PBS and stored at 4° C. until use. To demonstrate that microcapsules were functionalized by coupling of pectin-binding VHH, a binding experiment with microcapsules to *Arabidopsis thaliana* seeds was performed. For this purpose seeds were incubated with VHH-coupled microcapsules, blank microcapsules, or without microcapsules.

Binding of microcapsules to seeds was analyzed microscopically and fluorimetrically. Briefly, four *Arabidopsis thaliana* seeds per well were put in wells of a polypropylene 96-well plate (Nunc). Each condition was performed in quadruplicate consisting of four wells with four seeds per well each. Twenty-five µl of microcapsule suspensions with approximately 3.8E+04 microcapsules were added to each well and incubated on an ELISA shaking platform at room temperature for 1 hour. Unbound microcapsules were washed away from the seeds by careful pipetting to resuspend microcapsules and discarding supernatants. Three washes with PBS were performed. Seeds with bound microcapsules were transferred to 18-well µ-slides (Ibidi) and analyzed microscopically using epifluorescence. Uvitex OB was released from the bound microcapsules using ethanol, supernatants collected, and fluorescence measured. Fluorescence released from wells with just seeds was compared to wells with seeds incubated with blank microcapsules and wells with seeds incubated with microcapsules with coupled VHH 6D7. Average fluorescence measurements (standard deviation) were 30441 (±12934), 8722 (±4024), and 1784 (±238), for wells with seeds and microcapsules with VHH 6D7, wells with seeds and blank microcapsules, and wells with only seeds, respectively, demonstrating that VHH according to this invention can be used to bind microcapsules to plant seeds and that this binding substantially increases the amount of the microcapsule content that is retained to the plant seeds in comparison to microcapsules without VHH according to this invention.

Binding of VHH-Functionalized Microcapsules to Untreated Crop Seeds—

Microcapsule binding to crop seeds was investigated using rice, wheat and maize seeds and VHH-functionalized microcapsules with coupled VHH 7A7 and VHH 7A5. The fluorescent microcapsules with a core containing Uvitex OB were diluted to 1E+05 microcapsules/ml. Seeds and microcapsules were incubated with head-over-head rotation for 1 hour at room temperature in PBS or 1% BSA/PBS for rice and wheat, and maize seeds, respectively. Non-bound microcapsules were removed by washing with PBS. Seeds with bound microcapsules were analyzed for bound microcapsules on a macrozoom microscope system (Nikon). A DAPI filter was used to visualize the Uvitex OB microcapsules. Controls for VHH-coupled microcapsules included blank microcapsules to which no VHH were coupled. Significantly more microcapsules with VHH 7A7 or VHH 7A5 were found binding to rice and wheat seeds compared to blank microcapsules without VHH (see FIG. 5A for rice and FIG. 5B for wheat). Significantly more microcapsules with VHH 7A7 were found binding to maize seeds compared to blank microcapsules without VHH (see FIG. 5C). For quantitative measurements Uvitex OB was released from microcapsules bound to maize seeds. Three maize seeds per condition were incubated with microcapsules with coupled VHH 7A7. Microcapsule seed binding was performed as described before. Uvitex OB was released from the seed-bound microcapsules by incubation in 100% ethanol with vigorous shaking for 5 minutes. Supernatants were collected and in solution fluorescence was measured using a Fluostar Optima apparatus (BMG Labtech). Controls for VHH-coupled microcapsules included blank microcapsules to which no VHH were coupled and seeds without microcapsules. Microcapsule numbers bound to the seeds were calculated by means of measuring a standard concentration series of microcapsules. Calculated microcapsule numbers to maize seeds with coupled VHH 7A7 were 3.1E+02. Calculated microcapsule numbers for blank microcapsules or microcapsules with unrelated control VHH were 10 and 91, respectively, demonstrating that VHH according to this invention can be used to bind microcapsules to plant seeds and that this binding substantially increases the number of microcapsules that are retained to the plant seeds in comparison to microcapsules without VHH according to this invention.

Binding of VHH-Functionalized Microcapsules with Plant-Enhancing Agent to Untreated Crop Seeds—

Next it was investigated if VHH-functionalized microcapsules containing a plant-enhancing agent could be bound and retained to rice and wheat crop seeds. Therefore, the pyrethroid insecticide lambda-cyhalothrin was dissolved in benzyl-benzoate and encapsulated in functionalized poly-urea microcapsules to a final payload of 40%. These microcapsules were subsequently coupled with seed-binding proteins using similar methods as described in the first paragraph of this example. Ten rice and wheat seeds were separately incubated with microcapsule suspensions containing 1E+05 microcapsules/ml in PBS with head-over-head rotation for 1 hour at room temperature. Non-bound microcapsules were removed by washing with PBS. Washed seeds with bound microcapsules were transferred to glass vials and microcapsules were dissolved in acetone to release lambda cyhalothrin. Samples were diluted by addition of hexane containing #0.05% triphenylphosphate as internal standard. The amount of lambda cyhalothrin was determined by GC/MS-MS analysis in comparison with calibration solutions. 0.34 mg/kg lambda-cyhalothrin (corresponding to 1.3E+04 microcapsules) was measured on rice seeds treated with microcapsules coupled with VHH 6D7; while only 0.25 mg/kg lambda-cyhalothrin (corresponding to 9.6E+03 microcapsules) was detected on rice seeds treated with microcapsules coupled with a control VHH with a lower affinity for rice seeds. Similarly, 0.53 mg/kg lambda-cyhalothrin (corresponding to 2.0E+05 microcapsules) was measured on wheat seeds treated with microcapsules coupled with VHH 6D7, while only 0.43 mg/kg lambda-cyhalothrin (corresponding to 1.7E+04 microcapsules) was detected on wheat seeds treated with microcapsules coupled with a control VHH with a lower affinity for wheat seeds. Based on these results we conclude that VHH according to this invention are capable of efficiently binding and retaining a plant-enhancing agent (in casu: lambda-cyhalothrin), comprised in microcapsules, to seed surfaces, and that the amounts of plant-enhancing agent present on the seeds correlate with the binding affinity and specificity of the VHH used.

It will be clear to the person skilled in the art that the efficacy of a seed treatment composition hereof, comprising a plant-enhancing agent, can be evaluated as follows: first a composition for seed treatment hereof, comprising a plant-enhancing agent, is applied to one or more suitable seeds; subsequently, the treated seed is sown in the soil or in a pot containing soil and eventually the amount of the plant-enhancing agent present on the seed or in the seedling (in the case of a systemic plant-enhancing agent) is measured over time using suitable analytical methods. It will be appreciated that the amount of plant-enhancing agent present on the seed, treated with a composition hereof, is higher than the amount of plant-enhancing agent present on a seed, treated with a similar seed treatment composition, lacking a seed-binding protein hereof. Alternatively, the sown treated seed is exposed to soil-borne pathogens or the emergent seedling is exposed to pests or disease organisms and the damage caused to the emergent plant is monitored over time using any suitable method known to the person skilled in the art, including but not limited to visual inspection of the plant part that is affected. It will be appreciated that the amount of damage to the seedling, treated with a composition hereof, is lower than the amount of damage to the seedling, treated with a similar seed treatment composition, lacking a seed-binding protein hereof.

Example 9

Figure 6:
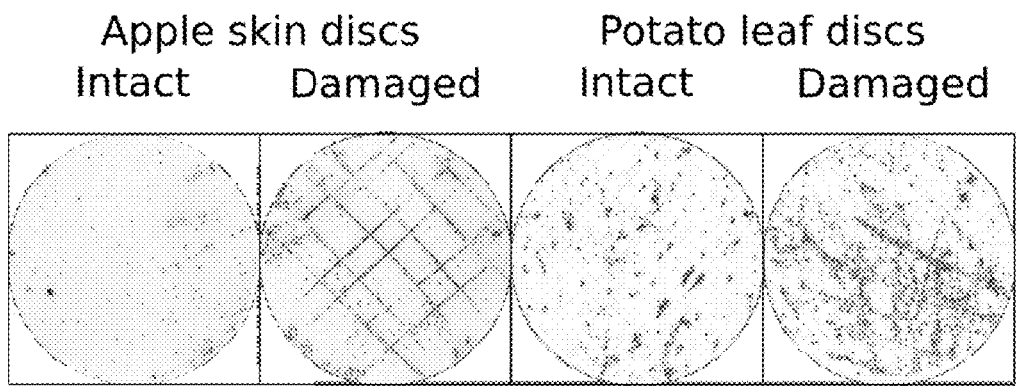

Binding of VHH Coupled to Microcapsules to Damaged Fruit and Wounded Plant Tissue A binding assay with apple skin discs was used to investigate binding of VHH-functionalized microcapsules to damaged fruit. A binding assay with potato leaf discs was used to investigate binding of VHH-functionalized microcapsules to wounded plant tissue. Discs of untreated apple skin were prepared by punching apple skin with a puncher tool. A series of apple skin discs was purposely damaged by making cuts on the outer surface of apple skin discs. Discs of untreated potato leaf (variety Désirée) were prepared by punching leaves with a puncher tool. A series of potato leaf discs was purposely damaged by making cuts into the upper surface of potato leaf discs. Binding of microcapsules with different coupled VHH was investigated in separate incubations for each condition. Apple skin discs or potato leaf discs were put facing up in wells of a multi-well plate. Microcapsules containing Uvitex OB were diluted to appropriate densities in 1% skimmed milk in PBS with 0.05%-TWEEN®-20. Microcapsules were added to the apple skin and potato leaf discs and settling of microcapsules and binding was allowed for 1 hour. Unbound microcapsules were removed by washing with PBS with 0.05%-TWEEN®-20. Apple skin and potato leaf discs were analyzed for bound microcapsules on a macrozoom microscope system (Nikon). A DAPI filter was used to visualize Uvitex OB microcapsules. Controls for VHH-coupled microcapsules included blank microcapsules to which no VHH were coupled and microcapsules to which unrelated VHH were coupled. Based on the results of the apple skin and potato leaf disc-binding assay with Uvitex OB microcapsules it was found that some of the VHH (e.g., VHH 6D7) hereof proved capable of binding and retaining microcapsules specifically to sites of damage on fruit or wounded tissue on plants (FIG. 6).

REFERENCES

Altschul S. F., T. L. Madden, A. A. Schäffer, J. Zhang, Z. Zhang, W. Miller and D. J. Lipman (1997). Gapped BLAST and PSI-BLAST: a new generation of protein database search programs. *Nucleic Acids Res.* 25:3389-3402.

Blake A. W., L. McCartney, J. Flint, D. N. Bolam, A. B. Boraston, H. J. Gilbert and J. P. Knox (2006). Understanding the biological rationale for the diversity of cellulose-directed carbohydrate-binding molecules in prokaryotic enzymes. *J. Biol. Chem.* 281:29321-29329.

Clausen M. H., W. G. Willatsz and J. P. Knox (2003). Synthetic methyl hexagalacturonate hapten inhibitors of anto-homogalacturonan monoclonal antibodies LM7, JIM5 and JIM7. *Carbohydr. Res.* 338:1997-1800.

Cozens-Roberts C., J. A. Quinn, and D. A. Lauffenburger (1990). Receptor-mediated cell attachment and detachment kinetics. *Biophys. J.* 58:857-872.

Dimitrov D. S. (2009). Engineered CH2 domains (nanoantibodies). mAbs 1, 26-28.

Fipula D. (2007). Antibody engineering and modification techniques. *Biomolecular Engineering* 24:201-205.

Fritz J. (2008). Cantilever biosensors. *Analyst* 133:855-863.

Goulao L. F. (2010). Pectin de-esterification and fruit softening: revisiting a classical hypothesis. *Stewart Postharvest Review* 6:1-12.

Harris B. (1999). Exploiting antibody-based technologies to manage environmental pollution. *Trends Biotechnol.* 17:290-296.

Huisman M. M. M., C. T. M. Fransen, J. P. Kamerling, J. F. G. Vliegenthart, H. A. Schols and A. G. J. Voragen (2001). The CDTA-soluble pectic substances from soybean meal are composed of rhamnogalacturonan and xylogalacturonan but not homogalacturonon. *Biopolymers* 58:279-294.

Knox J. P., P. J. Linstead, J. King, C. Cooper and K. Roberts (1990). Pectin esterification is spatially regulated both within cell walls and between developing tissues of root apices. *Planta* 181:512-521.

Knox J. P., P. J. Linstead, J. Peart, C. Cooper and K. Roberts (1991). Developmentally regulated epitopes of cell surface arabinogalactan proteins and their relation to root tissue pattern formation. *Plant J.* 1:317-326.

Kolmar H. (2008). Alternative binding proteins: biological activity and therapeutic potential of cysteine-knot miniproteins. *FEBS J.* 275:2684-2690.

Marcus S. E., Y. Verhertbruggen, C. Hervé, J. J. Ordaz-Ortiz, V. Farkas, H. L. Pedersen, W. G. Willats and J. P. Knox (2008). Pectic homogalacturonan masks abundant sets of xyloglucan epitopes in plant cell walls. *BMC Plant Biol.* 8:60.

Marquette C. A. and L. C. Blum (2006). State of the art and recent advances in immunoanalytical system. *Biosensors and Bioelectronics* 21:1424-1433.

McCartney L., S. E. Marcus and J. P. Knox (2005). Monoclonal antibodies to plant cell wall and arabinoxylans. *J. Histocham. Cytochem.* 53:543-546.

Moller I., I. Sørensen, A. J. Bernall, C. Blaukopf, K. Lee, J. Øbro, F. Pettolino, A. Roberts, J. D. Mikkelsen, J. P. Knox, A. Bacic and W. Willats (2007). High-throughput mapping of cell-wall polymers within and between plants using novel microarrays. *The Plant Journal* 50:1118-1128.

Nakamura A., H. Furuta, H. Maeda, T. Takao and Y. Nagamatsu (2002). Structural studies by stepwise enzymatic degradation of the main backbone of soybean soluble polysaccharides consisting of galacturonan and rhamnogalacturonan. *Biosci. Biotechnol. Biochem.* 66:1301-1313.

Nygren P-A. (2008). Alternative binding proteins: affibody-binding proteins developed from a small three-helix bundle scaffold. *FEBS J.* 275:2668-2676.

Øbro J., I. Sørensen, P. Derkx, C. T. Madsen, M. Drews, M. Willer, J. D. Mikkelsen and W. G. T. Willats (2009). High-throughput screening of *Erwinia chrysanthemi* pectin methylesterase variants using carbohydrate microarrays. *Proteomics* 9:1861-1868.

Pennell R. I., L. Janniche, P. Kjelborm, G. N. Scofield, J. M. Peart and K. Roberts (1991). Developmental regulation of plasma membrane arabinogalactan protein epitope in oilseed rape flowers. *Plant Cell* 3:1317-1326.

Skerra A. (2008). Alternative binding proteins: anticalins—harnessing the structural plasticity of the lipocalin ligand pocket to engineer novel binding activities. *FEBS J.* 275: 2677-2683.

Skottrup P. D., M. Nicolaisen and A. F. Justesen (2008). Towards on-site pathogen detection using antibody-based sensors. *Biosensors and Bioelectronics* 24:339-348.

Tramontano A., E. Bianchi, S. Venturini, F. Martin, A. Pessi and M. Sollazzo (1994). The making of the minibody: an engineered beta-protein for the display of conformationally constrained peptides. *J. Mol. Recognition.* 7:9-24.

Verhertbruggen Y., S. E. Marcus, A. Haeger, J. J. Ordaz-Oritz and J. P. Knox (2009). An extended set of monoclonal antibodies to pectic homogalacturan. *Carbohydr. Res.* 344: 1858-1862.

Willats W. G. and J. P. Knox (1999). Immunoprofiling of pectic polysaccharides. *Anal. Biochem.* 268:143-146.

Willats W. G., G. Limberg, H. C. Buchholt, G. J. van Alebeek, J. Benen, T. M. Chritensten, J. Visser, A. Voragen, J. D. Mikkelsen and J. P. Knox (2000). Analysis of pectic epitopes recognized by hybridoma and phage display monoclonal antibodies using defined oligosaccharides, polysaccharides and enzymatic degradation. *Carbohydr. Res.* 327:309-320.

Yates E. A., J. F. Valdor, S. M. Haslam, H. R. Morris, A. Dell, W. Mackie and J. P. Knox (1996). Characterization of carbohydrate structural features recognized by anti-arabinogalactan-protein monoclonal antibodies. *Glycobiology* 6:131-139.

Zayas P. T., G. Geissler and F. Hernandez (20070. Chemical oxygen demand reduction in coffee wastewater through chemical flocculation and advanced oxidation process. *J. Environ. Science* 19:300-305.

Zheng M., R. Toledo and L. Wicker (1999). Effect of phosphate and pectin on quality and shelf-life of marinated chicken breast. *J. Food Quality* 22:553-564.

---

What is claimed is:

1. A composition for plant seed treatment, the composition comprising a plant seed-binding protein;
   wherein the plant seed-binding protein is an antigen-binding protein comprising a VHH;
   wherein the VHH binds to pectin; and
   wherein the VHH is able to bind to a plant seed coat.

2. The composition of claim 1, wherein the plant seed-binding protein is able to bind a plant-enhancing agent to the plant seed coat.

3. The composition of claim 1, wherein the plant seed-binding protein is able to bind a carrier onto the plant seed coat.

4. The composition of claim 1, wherein said pectin comprises low esterified homogalacturan.

5. A composition for plant seed treatment, the composition comprising a plant seed-binding protein;
   wherein the plant seed-binding protein is an antigen-binding protein comprising a VHH;
   wherein the VHH is able to bind to a plant seed coat; and,
   wherein the VHH comprises a peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

6. A method for treating a plant seed, said method comprising:
   preparing the composition of claim 1; and
   applying said composition to the plant seed.

7. A method comprising:
   treating a seed with the composition of claim 1; and
   sowing the treated seed,
   wherein the composition of claim 1 further comprises an agent that protects the plant seed and/or the emergent seedling against seed-borne and/or soil-borne pathogens; and/or
   wherein the composition of claim 1 further comprises an agent that protects the plant growing from the treated seed and/or in the immediate vicinity of the treated seed against damage caused by pests and/or disease; and/or
   wherein the composition of claim 1 further comprises an agent that protects the plant seed and/or the plant growing from the treated seed and/or in the immediate vicinity of the treated seed against damage caused by weeds and/or other undesired plants; and/or
   wherein the composition of claim 1 further comprises an agent that enhances the yield of the plant growing from the treated seed and/or in the immediate vicinity of the treated seed.

8. A seed-binding protein, wherein said seed-binding protein is an antigen-binding protein comprising
   a VHH;
   wherein the VHH binds to pectin; and
   wherein the antigen-binding protein binds to a plant seed coat.

9. A seed-binding protein, wherein the seed-binding protein is an antigen-binding protein comprising four framework regions and three complementarity-determining regions;
   wherein the antigen-binding protein comprises a VHH; and,
   wherein the VHH comprises a peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

10. The seed-binding protein of claim 8, wherein said pectin is low esterified homogalacturan.

11. The seed-binding protein of claim 8, wherein said pectin is in solution.

12. The seed-binding protein of claim 8, wherein said pectin is comprised in a solid surface.

13. The seed-binding protein of claim 8, wherein said pectin is comprised in vegetable material.

14. A method of binding a plant-enhancing agent to a plant seed, the method comprising:
   binding a plant-enhancing agent to a plant seed through the seed binding protein of claim 8.

15. The method of claim 14, further comprising measuring the presence and/or concentration of a polysaccharide in a sample.

16. The method of claim 14, further comprising purifying a polysaccharide from a sample.

17. An agrochemical composition, comprising at least one seed-binding protein of claim 8.

18. A kit of parts for the detection and/or determination of the concentration of one or more polysaccharides, the kit of parts comprising at least one seed-binding protein of claim 8.

19. A biosensor for the detection and/or determination of the concentration of one or more polysaccharides, said biosensor comprising at least one seed-binding protein of claim 8.

20. A targeting agent able to bind a compound to a plant seed, wherein said targeting agent comprises at least one seed-binding protein of claim 8.

21. A method of binding a plant-enhancing agent to a plant seed, the method comprising:
   binding a plant-enhancing agent to a plant or plant part through the targeting agent of claim 20.

22. A method of modifying plant cell wall components, the method comprising:
   binding a plant cell wall modifying agent to a plant cell wall through the targeting agent of claim 20.

23. An agrochemical composition comprising the targeting agent of claim 20.

24. The agrochemical composition of claim 23, wherein said composition is a composition for seed treatment.

25. The composition of claim 1, further comprising:
   a plant-enhancing agent bonded to the plant seed-binding protein,
   wherein the plant-enhancing agent is selected from the group consisting of a disinfectant, a disinfestation agent, a micro-organism, a plant growth regulator, a nutrient, a plant hormones, a mineral, a germination stimulant, a humectant, a stress protector, a plant inducers, and any combination thereof.

26. The seed-binding protein of claim 8, further comprising:
   a plant-enhancing agent bonded to the seed-binding protein,
   wherein the plant-enhancing agent is selected from the group consisting of a disinfectant, a disinfestation agent, a micro-organism, a plant growth regulator, a nutrient, a plant hormones, a mineral, a germination stimulant, a humectant, a stress protector, a plant inducers, and any combination thereof.

* * * * *

SEQUENCE LISTING

```
<160> NUMBER OF SEQ ID NOS: 18

<210> SEQ ID NO 1
<211> LENGTH: 115
<212> TYPE: PRT
<213> ORGANISM: Lama glama
<220> FEATURE:
<221> NAME/KEY: MISC_FEATURE
<223> OTHER INFORMATION: 6B5
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(104)
<223> OTHER INFORMATION: CDR3
<220> FEATURE:
<221> NAME/KEY: MISC_FEATURE
<222> LOCATION: (105)..(115)
<223> OTHER INFORMATION: FR4

<400> SEQUENCE: 1

Gln Val Gln Leu Gln Glu Ser Gly Gly Gly Leu Val Gln Pro Gly Gly
1               5                   10                  15

Ser Leu Arg Leu Ser Cys Val Ala Ser Gly Phe Thr Phe Ser Ser Arg
            20                  25                  30

Thr Met Asn Trp Val Arg Gln Ala Pro Gly Lys Gly Leu Glu Trp Val
        35                  40                  45

Ser Thr Leu Asn Trp Asp Gly Asp Ser Ala Ser Tyr Thr Asp Ser Val
```

```
                50              55              60
Lys Gly Arg Phe Thr Val Ser Arg Asp Asn Ala Lys Asn Thr Leu Tyr
 65                      70                  75                  80

Leu Gln Met Asn Ser Leu Lys Ala Glu Asp Thr Ala Val Tyr Tyr Cys
                     85                  90                  95

Ser Ile Gly Thr Ile Arg Gly Ser Arg Gly Gln Gly Thr Gln Val Thr
                100                 105                 110

Val Ser Ser
        115

<210> SEQ ID NO 2
<211> LENGTH: 125
<212> TYPE: PRT
<213> ORGANISM: Lama glama
<220> FEATURE:
<221> NAME/KEY: MISC_FEATURE
<223> OTHER INFORMATION: 6D7
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(114)
<223> OTHER INFORMATION: CDR3
<220> FEATURE:
<221> NAME/KEY: MISC_FEATURE
<222> LOCATION: (115)..(125)
<223> OTHER INFORMATION: FR4

<400> SEQUENCE: 2

Gln Val Gln Leu Gln Glu Ser Gly Gly Gly Trp Val Gln Ala Gly Gly
 1               5                  10                  15

Ser Leu Arg Leu Ser Cys Ala Ala Ser Gly Pro Thr Phe Ser Thr Tyr
             20                  25                  30

Val Met Ala Trp Phe Arg Gln Ala Pro Gly Lys Glu Arg Glu Phe Val
         35                  40                  45

Ala Gly Ile Thr Arg Ser Gly Ala Val Pro Arg Tyr Ala Asp Ser Val
     50                  55                  60

Lys Gly Arg Phe Ser Val Ser Arg Asp Asn Ala Arg Asn Met Val Tyr
 65                      70                  75                  80

Leu Gln Met Asn Ser Leu Arg Pro Glu Asp Thr Ala Val Tyr Tyr Cys
                     85                  90                  95

Ala Ala Arg Ser Leu Ser Gly Arg Val Ala Gly Gln Glu Tyr Glu Tyr
                100                 105                 110

Asp Tyr Trp Gly Gln Gly Thr Gln Val Thr Val Ser Ser
        115                 120                 125

<210> SEQ ID NO 3
```

```
<211> LENGTH: 115
<212> TYPE: PRT
<213> ORGANISM: Lama glama
<220> FEATURE:
<221> NAME/KEY: MISC_FEATURE
<223> OTHER INFORMATION: 6D11
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(104)
<223> OTHER INFORMATION: CDR3
<220> FEATURE:
<221> NAME/KEY: MISC_FEATURE
<222> LOCATION: (105)..(115)
<223> OTHER INFORMATION: FR4

<400> SEQUENCE: 3

Gln Val Gln Leu Gln Glu Phe Gly Gly Gly Leu Val Gln Pro Gly Gly
1               5                   10                  15

Ser Leu Arg Leu Ser Cys Val Ala Ser Gly Phe Thr Phe Ser Ser Arg
            20                  25                  30

Thr Met Asn Trp Val Arg Gln Ala Pro Gly Lys Gly Leu Glu Trp Val
        35                  40                  45

Ser Thr Leu Asn Arg Asp Gly Asp Ser Ala Ser Tyr Thr Asp Ser Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ser Ile Gly Thr Ile Arg Gly Ser Arg Gly Gln Gly Thr Gln Val Thr
            100                 105                 110

Val Ser Ser
        115

<210> SEQ ID NO 4
<211> LENGTH: 115
<212> TYPE: PRT
<213> ORGANISM: Lama glama
<220> FEATURE:
<221> NAME/KEY: MISC_FEATURE
<223> OTHER INFORMATION: 6F2
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
```

```
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(104)
<223> OTHER INFORMATION: CDR3
<220> FEATURE:
<221> NAME/KEY: MISC_FEATURE
<222> LOCATION: (105)..(115)
<223> OTHER INFORMATION: FR4

<400> SEQUENCE: 4

Gln Val Gln Leu Gln Glu Ser Gly Gly Gly Leu Val Gln Pro Gly Gly
 1               5                   10                  15

Ser Leu Arg Leu Ser Cys Val Ala Ser Gly Phe Thr Phe Ser Ser Arg
            20                  25                  30

Thr Met Asn Trp Val Arg Gln Ala Pro Gly Lys Gly Leu Glu Trp Val
        35                  40                  45

Ser Thr Leu Asn Arg Asp Gly Asp Ser Ala Ser Tyr Thr Asp Ser Val
    50                  55                  60

Lys Gly Arg Phe Thr Val Ser Arg Asp Asn Ala Lys Asn Thr Leu Tyr
65                  70                  75                  80

Leu Gln Met Ser Ser Leu Lys Ala Glu Asp Thr Ala Val Tyr Tyr Cys
                85                  90                  95

Ser Ile Gly Thr Ile Arg Gly Ser Arg Gly Gln Gly Thr Gln Val Thr
            100                 105                 110

Val Ser Ser
        115

<210> SEQ ID NO 5
<211> LENGTH: 115
<212> TYPE: PRT
<213> ORGANISM: Lama glama
<220> FEATURE:
<221> NAME/KEY: MISC_FEATURE
<223> OTHER INFORMATION: 6H4
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(104)
<223> OTHER INFORMATION: CDR3
<220> FEATURE:
<221> NAME/KEY: MISC_FEATURE
```

```
<222> LOCATION: (105)..(115)
<223> OTHER INFORMATION: FR4

<400> SEQUENCE: 5

Gln Val Gln Leu Gln Glu Ser Gly Gly Gly Leu Val Gln Pro Gly Gly
1               5                   10                  15

Ser Leu Arg Leu Ser Cys Val Ala Ser Gly Phe Thr Phe Ser Ser Arg
            20                  25                  30

Thr Met Asn Trp Val Arg Gln Ala Pro Gly Lys Gly Leu Glu Trp Val
        35                  40                  45

Ser Thr Leu Asn Arg Asn Gly Asp Ser Ala Ser Tyr Thr Asp Ser Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ser Ile Gly Thr Ile Arg Gly Ser Arg Gly Gln Gly Thr Gln Val Thr
            100                 105                 110

Val Ser Ser
        115

<210> SEQ ID NO 6
<211> LENGTH: 115
<212> TYPE: PRT
<213> ORGANISM: Lama glama
<220> FEATURE:
<221> NAME/KEY: MISC_FEATURE
<223> OTHER INFORMATION: 7A5
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(104)
<223> OTHER INFORMATION: CDR3
<220> FEATURE:
<221> NAME/KEY: MISC_FEATURE
<222> LOCATION: (105)..(115)
<223> OTHER INFORMATION: FR4

<400> SEQUENCE: 6

Gln Val Gln Leu Gln Glu Ser Gly Gly Gly Leu Val Gln Pro Gly Gly
1               5                   10                  15

Ser Leu Arg Leu Ser Cys Val Ala Ser Gly Phe Thr Phe Ser Ser Arg
            20                  25                  30

Thr Met Asn Trp Val Arg Gln Ala Pro Gly Lys Gly Leu Glu Trp Val
        35                  40                  45

Ser Thr Leu Asn Arg Asp Gly Asp Ser Ala Ser Tyr Thr Asp Ser Val
    50                  55                  60
```

```
Lys Gly Arg Phe Thr Val Ser Arg Asp Asn Ala Lys Asn Thr Leu Tyr
 65                  70                  75                  80

Leu Gln Met Asn Ser Leu Lys Ala Glu Asp Thr Ala Val Tyr Tyr Cys
                 85                  90                  95

Ser Ile Gly Thr Ile Arg Gly Ser Arg Gly Gln Gly Thr Gln Val Thr
            100                 105                 110

Val Ser Ser
        115

<210> SEQ ID NO 7
<211> LENGTH: 124
<212> TYPE: PRT
<213> ORGANISM: Lama glama
<220> FEATURE:
<221> NAME/KEY: MISC_FEATURE
<223> OTHER INFORMATION: 7A7
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(113)
<223> OTHER INFORMATION: CDR3
<220> FEATURE:
<221> NAME/KEY: MISC_FEATURE
<222> LOCATION: (114)..(124)
<223> OTHER INFORMATION: FR4

<400> SEQUENCE: 7

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Arg Thr Phe Ser Arg Tyr
             20                  25                  30

Ala Met Gly Trp Phe Arg Gln Ala Pro Gly Ala Asp Arg Glu Phe Val
         35                  40                  45

Ala Ala Val Ser Trp Ser Gly Arg Thr Tyr Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Ala Glu Asp Thr Ala Val Tyr Tyr Cys
                 85                  90                  95

Thr Pro Val Tyr Gly Thr Ala Pro Thr Thr Val Arg Ser Arg Ser Asp
            100                 105                 110

Tyr Trp Gly Gln Gly Thr Gln Val Thr Val Ser Ser
        115                 120

<210> SEQ ID NO 8
<211> LENGTH: 124
```

```
<212> TYPE: PRT
<213> ORGANISM: Lama glama
<220> FEATURE:
<221> NAME/KEY: MISC_FEATURE
<223> OTHER INFORMATION: 7E9
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(113)
<223> OTHER INFORMATION: CDR3
<220> FEATURE:
<221> NAME/KEY: MISC_FEATURE
<222> LOCATION: (114)..(124)
<223> OTHER INFORMATION: FR4

<400> SEQUENCE: 8

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Arg Tyr
            20                  25                  30

Ala Met Gly Trp Phe Arg Gln Ala Pro Gly Ala Asp Arg Glu Phe Val
        35                  40                  45

Ala Ala Val Ser Trp Ser Gly Arg Thr Tyr Tyr Ala Gly Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Thr Pro Val Tyr Gly Thr Ala Pro Thr Thr Val Arg Ser Arg Ser Asp
            100                 105                 110

Tyr Trp Gly Gln Gly Thr Gln Val Thr Val Ser Ser
            115                 120

<210> SEQ ID NO 9
<211> LENGTH: 124
<212> TYPE: PRT
<213> ORGANISM: Lama glama
<220> FEATURE:
<221> NAME/KEY: MISC_FEATURE
<223> OTHER INFORMATION: 8A4
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
```

```
<223> OTHER INFORMATION: FR2
<220> FEATURE:
<221> NAME/KEY: MISC_FEATURE
<222> LOCATION: (50)..(65)
<223> OTHER INFORMATION: CDR2
<220> FEATURE:
<221> NAME/KEY: MISC_FEATURE
<222> LOCATION: (66)..(97)
<223> OTHER INFORMATION: FR3
<220> FEATURE:
<221> NAME/KEY: MISC_FEATURE
<222> LOCATION: (98)..(113)
<223> OTHER INFORMATION: CDR3
<220> FEATURE:
<221> NAME/KEY: MISC_FEATURE
<222> LOCATION: (114)..(120)
<223> OTHER INFORMATION: FR4

<400> SEQUENCE: 9

Gln Val Gln Leu Gln Glu Ser Gly Gly Gly Leu Val Gln Ala Gly Glu
 1               5                  10                  15

Ser Leu Arg Leu Ala Cys Thr Ala Ser Gly Ser Ile Phe Ser Ile Asn
            20                  25                  30

Gly Met Gly Trp Tyr Arg Gln Ala Pro Gly Lys Gln Arg Asp Leu Val
        35                  40                  45

Ala Ala Ile Ala Ser Gly Gly Ser Thr Thr Tyr Gly Asp Ala Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Lys Glu Val Arg Ser Thr Glu Thr Ser Tyr Arg Val Gln Asn Asn
           100                 105                 110

Tyr Trp Gly Gln Gly Thr Gln Val Thr Val Ser Ser
           115                 120

<210> SEQ ID NO 10
<211> LENGTH: 124
<212> TYPE: PRT
<213> ORGANISM: Lama glama
<220> FEATURE:
<221> NAME/KEY: MISC_FEATURE
<223> OTHER INFORMATION: 8D6
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(65)
<223> OTHER INFORMATION: CDR2
<220> FEATURE:
<221> NAME/KEY: MISC_FEATURE
<222> LOCATION: (66)..(97)
<223> OTHER INFORMATION: FR3
<220> FEATURE:
<221> NAME/KEY: MISC_FEATURE
<222> LOCATION: (98)..(113)
<223> OTHER INFORMATION: CDR3
<220> FEATURE:
<221> NAME/KEY: MISC_FEATURE
<222> LOCATION: (114)..(120)
```

-continued

<223> OTHER INFORMATION: FR4

<400> SEQUENCE: 10

Gln Val Gln Leu Gln Glu Ser Gly Gly Gly Leu Val Gln Ala Gly Glu
1               5                   10                  15

Ser Leu Arg Leu Ala Cys Thr Ala Ser Gly Ser Ile Phe Ser Ile Asn
            20                  25                  30

Gly Met Gly Trp Tyr Arg Gln Ala Pro Gly Lys Gln Arg Asp Leu Val
        35                  40                  45

Ala Ala Ile Ala Ser Gly Gly Ser Thr Thr Tyr Gly Asp Ala Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Lys Glu Val Arg Ser Thr Gly Thr Ser Tyr Arg Val Gln Asn Asn
            100                 105                 110

Tyr Trp Gly Gln Gly Thr Gln Val Thr Val Ser Ser
        115                 120

<210> SEQ ID NO 11
<211> LENGTH: 128
<212> TYPE: PRT
<213> ORGANISM: Lama glama
<220> FEATURE:
<221> NAME/KEY: MISC_FEATURE
<223> OTHER INFORMATION: 12C3
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(99)
<223> OTHER INFORMATION: FR3
<220> FEATURE:
<221> NAME/KEY: MISC_FEATURE
<222> LOCATION: (100)..(118)
<223> OTHER INFORMATION: CDR3
<220> FEATURE:
<221> NAME/KEY: MISC_FEATURE
<222> LOCATION: (119)..(121)
<223> OTHER INFORMATION: FR4

<400> SEQUENCE: 11

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Asn Ser Tyr
            20                  25                  30

Ala Met Gly Trp Phe Arg Gln Ala Pro Gly Lys Glu Arg Glu Phe Val
        35                  40                  45

Ala Ala Ile Thr Arg Ser Gly Gly Ser Thr Phe Tyr Glu Asp Leu Val
    50                  55                  60

-continued

```
Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Phe Cys
             85                  90                  95

Ala Ala Lys Ala Gln Asp Leu Arg Tyr Asn Ser Arg Ser Tyr Tyr Tyr
        100                 105                 110

Thr Asp Tyr Asp Tyr Trp Gly Gln Gly Thr Gln Val Thr Val Ser Ser
        115                 120                 125
```

```
<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
gtcctggctg ctcttctaca agg                                        23

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
cctggctgct cttctacaag gtg                                        23

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ggtacgtgct gttgaactgt tcc                                        23

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
gatgtgcagc tgcaggagtc tggrggagg                                  29

<210> SEQ ID NO 16
<211> LENGTH: 35
<212> TYPE: DNA
<213> ORGANISM: Artificial Sequence
<220> FEATURE:
<223> OTHER INFORMATION: Primer

<400> SEQUENCE: 16
ggactagtgc ggccgctgga gacggtgacc tgggt                           35

<210> SEQ ID NO 17
<211> LENGTH: 20
<212> TYPE: DNA
<213> ORGANISM: Artificial Sequence
<220> FEATURE:
<223> OTHER INFORMATION: Primer
```

```
-continued

<400> SEQUENCE: 17
ttatgcttcc ggctcgtatg                                                    20

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
ccacagacag ccctcatag                                                     19
```